(12) United States Patent
Vogt et al.

(10) Patent No.: US 11,241,266 B2
(45) Date of Patent: *Feb. 8, 2022

(54) DEVICE FOR MIXING A BONE CEMENT WITH HOLLOW SPACE FOR MONOMER TRANSFER

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 157 days.

This patent is subject to a terminal disclaimer.

(21) Appl. No.: 16/705,881

(22) Filed: Dec. 6, 2019

(65) Prior Publication Data

US 2020/0179023 A1 Jun. 11, 2020

(30) Foreign Application Priority Data

Dec. 7, 2018 (DE) ...................... 10 2018 131 266.0

(51) Int. Cl.
*A61B 17/88* (2006.01)
*A61C 5/62* (2017.01)
(Continued)

(52) U.S. Cl.
CPC ............ *A61B 17/8833* (2013.01); *A61C 5/62* (2017.02); *A61C 5/64* (2017.02); *A61B 17/8825* (2013.01);
(Continued)

(58) Field of Classification Search
CPC ........ A61B 17/8802; A61B 2017/8838; A61C 5/62; A61C 5/64
See application file for complete search history.

(56) References Cited

U.S. PATENT DOCUMENTS 2,446,501 A 12/1944 Weber
2,591,046 A 4/1952 Brown
(Continued)

FOREIGN PATENT DOCUMENTS

CN 108421132 8/2018
DE 3640279 6/1987
(Continued)

OTHER PUBLICATIONS

Charnley, J., "Anchorage of the Femoral Head Prosthesis of the Shaft of the Femur," The Journal of Bone and Joint Surgery, 42 B, No. 1, pp. 28-30 (Feb. 1960).
(Continued)

*Primary Examiner* — Nicholas W Woodall
(74) *Attorney, Agent, or Firm* — Dicke, Billig & Czaja, PLLC

(57) ABSTRACT

One aspect relates to a device for the production of a bone cement dough from a monomer liquid and a cement powder comprising a cartridge with an internal space; a cartridge head with a dispensing opening; a conveying plunger that is supported in the internal space of the cartridge such that it is pushable in the direction of the dispensing opening; a dispensing plunger between the dispensing opening and the conveying plunger that is supported in the internal space of the cartridge such that it is pushable in the direction of the dispensing opening; a first hollow space, in which the cement powder is arranged; a second hollow space that is bordered by the dispensing plunger and the conveying plunger; a rear-side part of the internal space of the cartridge; and a conducting means that connects the second hollow space to the rear-side part of the internal space of the cartridge such as to bypass the conveying plunger and be permeable to the monomer liquid. The conducting means can be closed by the conveying plunger with respect to the (Continued)

second hollow space by shifting the conveying plunger in the direction of the dispensing plunger, and a feedthrough in the dispensing plunger that connects the first hollow space and the second hollow space such as to be permeable to the monomer liquid.

21 Claims, 9 Drawing Sheets

(51) Int. Cl.
  *A61C 5/64* (2017.01)
  *A61B 17/00* (2006.01)
(52) U.S. Cl.
  CPC ............... *A61B 2017/00526* (2013.01); *A61B 2017/8838* (2013.01)

(56) References Cited

U.S. PATENT DOCUMENTS

| | | | |
|---|---|---|---|
| 2,754,590 A * | 7/1956 | Cohen | A61C 5/50 |
| | | | 433/90 |
| 2,869,543 A | 1/1959 | Ratcliff et al. | |
| 3,164,303 A | 1/1965 | Trautmann | |
| 3,464,412 A | 9/1969 | Schwartz | |
| 3,684,136 A * | 8/1972 | Baumann | B65D 81/3255 |
| | | | 222/386 |
| 3,739,947 A * | 6/1973 | Baumann | A61M 5/284 |
| | | | 222/136 |
| 4,391,590 A * | 7/1983 | Dougherty | B05C 17/00596 |
| | | | 433/90 |
| 4,648,532 A * | 3/1987 | Green | A61C 5/66 |
| | | | 222/82 |
| 4,671,263 A | 6/1987 | Draenert | |
| 4,758,096 A | 7/1988 | Gunnarsson | |
| 4,898,580 A | 2/1990 | Crowley | |
| 4,968,299 A | 11/1990 | Ahlstrand et al. | |
| 4,972,969 A * | 11/1990 | Randklev | B65D 81/32 |
| | | | 206/219 |
| 4,973,168 A | 11/1990 | Chan | |
| 5,026,283 A * | 6/1991 | Osanai | A61C 5/64 |
| | | | 206/222 |
| 5,100,241 A | 3/1992 | Chan | |
| 5,344,232 A | 9/1994 | Nelson et al. | |
| 5,551,778 A | 9/1996 | Hauke et al. | |
| 5,586,821 A | 12/1996 | Bonitati et al. | |
| 5,588,745 A | 12/1996 | Tanaka et al. | |
| 5,624,184 A | 4/1997 | Chan | |
| 5,779,356 A | 7/1998 | Chan | |
| 5,971,953 A | 10/1999 | Bachynsky | |
| 5,997,544 A | 12/1999 | Nies et al. | |
| 6,017,349 A | 1/2000 | Heller et al. | |
| 6,033,105 A | 3/2000 | Barker et al. | |
| 6,120,174 A | 9/2000 | Hoag et al. | |
| 6,386,872 B1 * | 5/2002 | Mukasa | A61C 5/64 |
| | | | 206/219 |
| 6,544,233 B1 | 4/2003 | Fukui et al. | |
| 6,709,149 B1 | 3/2004 | Tepic | |
| 6,869,284 B2 * | 3/2005 | Aoyagi | A61C 5/62 |
| | | | 433/90 |
| 6,935,541 B1 | 8/2005 | Campbell et al. | |
| 7,073,936 B1 | 7/2006 | Jonsson | |
| 8,128,276 B2 | 3/2012 | Axelsson et al. | |
| 8,690,419 B2 | 4/2014 | Faccioli et al. | |
| 8,747,866 B2 | 6/2014 | Vogt et al. | |
| 8,757,866 B2 | 6/2014 | Vogt et al. | |
| 8,968,000 B2 * | 3/2015 | Leiner | A61C 5/64 |
| | | | 433/90 |
| 9,247,979 B2 | 2/2016 | Faccioli et al. | |
| 9,326,829 B2 * | 5/2016 | Kojima | A61C 5/64 |
| 9,775,690 B2 | 10/2017 | Cheetham | |
| 2004/0074927 A1 | 4/2004 | Lafond | |
| 2005/0222538 A1 | 10/2005 | Embry et al. | |
| 2006/0274601 A1 | 12/2006 | Seaton | |
| 2014/0192611 A1 | 7/2014 | Sasaki et al. | |
| 2014/0254303 A1 | 9/2014 | McArthur et al. | |
| 2014/0269147 A1 | 9/2014 | Click et al. | |
| 2016/0045283 A1 | 2/2016 | Boehm et al. | |
| 2017/0252715 A1 | 9/2017 | Vogt et al. | |
| 2018/0132917 A1 | 5/2018 | Vogt et al. | |
| 2018/0132919 A1 | 5/2018 | Vogt et al. | |
| 2018/0256233 A1 | 9/2018 | Vogt et al. | |
| 2018/0289406 A1 | 10/2018 | Vogt et al. | |
| 2018/0310974 A1 | 11/2018 | Vogt et al. | |
| 2018/0333176 A1 | 11/2018 | Vogt et al. | |
| 2019/0216516 A1 | 7/2019 | Vogt et al. | |
| 2020/0129215 A1 | 4/2020 | Vogt | |
| 2020/0129216 A1 | 4/2020 | Vogt | |
| 2020/0179024 A1 | 6/2020 | Vogt et al. | |

FOREIGN PATENT DOCUMENTS

| | | |
|---|---|---|
| DE | 69812726 | 2/2004 |
| DE | 20 2005 010 206 | 9/2005 |
| DE | 10 2009 031 178 | 9/2010 |
| DE | 102009031178 | 9/2010 |
| DE | 102016121607 | 5/2018 |
| DE | 10 2018 101 041 | 7/2019 |
| EP | 0 692 229 | 1/1996 |
| EP | 0692229 | 1/1996 |
| EP | 0 796 653 | 9/1997 |
| EP | 0796653 | 9/1997 |
| EP | 1 005 901 | 6/2000 |
| EP | 1005901 | 6/2000 |
| EP | 1 016 452 | 7/2000 |
| EP | 1 020 167 | 7/2000 |
| EP | 1016452 | 7/2000 |
| EP | 1020167 | 7/2000 |
| EP | 1093826 | 4/2001 |
| EP | 1 886 647 | 2/2008 |
| EP | 1886647 | 2/2008 |
| EP | 1883379 | 9/2013 |
| EP | 3320870 | 5/2018 |
| JP | 2011-067265 | 4/2011 |
| WO | 94/26403 | 11/1994 |
| WO | 99/67015 | 12/1999 |
| WO | 00/35506 | 6/2000 |
| WO | 2006/123205 | 11/2006 |
| WO | 2011/089480 | 7/2011 |
| WO | 2012/115022 | 8/2012 |

OTHER PUBLICATIONS

Kuhn, Klaus-Dieter, "Bone Cements," Springer-Verlag, pp. 9 (2000).
Non-Final Office Action dated Aug. 10, 2021 in U.S. Appl. No. 16/655,610.

* cited by examiner

DEVICE FOR MIXING A BONE CEMENT WITH HOLLOW SPACE FOR MONOMER TRANSFER

CROSS-REFERENCE TO RELATED APPLICATION

This Utility Patent Application claims priority to German Application No. 10 2018 131 266.0 filed on Dec. 7, 2018, which is incorporated herein by reference.

TECHNICAL FIELD

One embodiment relates to a device for production of a bone cement dough from a monomer liquid and a cement powder as starting components of the bone cement dough, and for dispensing of the mixed bone cement dough.

One embodiment also relates to a method for production of a bone cement dough, in particular of a pasty polymethylmethacrylate bone cement dough, with the device.

BACKGROUND

The subject matter of one embodiment specifically is a device for separate storage of the cement powder and the monomer liquid of polymethylmethacrylate bone cements, for subsequent mixing of the cement powder with the monomer liquid in order to produce a bone cement dough, and for dispensing the mixed bone cement dough. Preferably, the device according to one embodiment is a full-prepacked mixing system. Particularly in one embodiment, the device is designed appropriately such that mixed bone cement dough can be dispensed without the use of a separate extrusion device.

Polymethylmethacrylate (PMMA) bone cements are based on the pioneering work of Sir Charnley (Charnley, J.: Anchorage of the femoral head prosthesis of the shaft of the femur. J. Bone Joint Surg. 42 (1960) 28-30.). Conventional polymethylmethacrylate bone cements (PMMA bone cements) are made from a powdered component and a liquid monomer component (K.-D. Kühn: Knochenzemente für die Endoprothetik: Ein aktueller Vergleich der physikalischen and chemischen Eigenschaften handelsüblicher PMMA-Zemente. Springer-Verlag Berlin Heidelberg N.Y., 2001). The monomer component generally contains the monomer, methylmethacrylate, and an activator (N,N-dimethyl-p-toluidine) dissolved therein. The powder component, also called cement powder or bone cement powder, comprises one or more polymers that are produced through polymerisation, in one embodiment suspension polymerisation, based on methylmethacrylate and co-monomers, such as styrene, methylacrylate or similar monomers, a radiopaquer, and the initiator, dibenzoylperoxide. Mixing the powder component and the monomer component, swelling of the polymers of the powder component in the methylmethacrylate generates dough that can be shaped plastically and is the actual bone cement or bone cement dough. During the mixing of powder component and monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the bone cement dough increases until the bone cement dough solidifies.

PMMA bone cements can be mixed by mixing the cement powder and the monomer liquid in suitable mixing beakers with the aid of spatulas. This can lead to air bubbles being enclosed in the bone cement dough, which can have a negative effect on the mechanical properties of the cured bone cement.

A large number of vacuum cementing systems has been described for preventing air inclusions in bone cement dough of which the following shall be specified here for exemplary purposes: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, U.S. Pat. No. 5,344,232 A.

Cementing systems, in which both the cement powder and the monomer liquid are already packed in separate compartments of the mixing devices and are mixed with each other in the cementing system only right before application of the cement, are a development of cementing technology. The closed full-prepacked mixing systems have been proposed in EP 0 692 229 A1, DE 10 2009 031 178 B3, U.S. Pat. Nos. 5,997,544 A, 6,709,149 B1, DE 698 12 726 T2, EP 0 796 653 A2, U.S. Pat. No. 5,588,745 A, US 2018/333 176 A1, US 2018/310 974 A1, US 2018/289 406 A1, US 2018/132 919 A1, US 2018/132 917 A1, and US 2018/256 233 A1.

Patent DE 10 2009 031 178 B3 discloses a storage and mixing device as a full-prepacked mixing system, in which the starting components required for production of the bone cement dough are stored already in the storage and mixing device and can be combined and mixed in the storage and mixing device. The storage and mixing device comprises a two-part dispensing plunger for closing a cement cartridge. A combination of a gas-permeable sterilisation plunger and a gas-impermeable sealing plunger is used in this context.

After mixing the cement powder with the liquid monomer component, polymethylmethacrylate bone cements are applied in their non-cured pasty state in the form of a bone cement dough. If mixing devices are used with powder-liquid cements, the bone cement dough is situated in a cartridge. During the application of the conventional PMMA bone cements, the bone cement dough produced after mixing the two starting components is extruded with the aid of manually operable extrusion devices. The bone cement dough is squeezed from the cartridge by moving a dispensing plunger.

These simple mechanical extrusion devices utilise, in particular, clamp rods that are driven by a manually-actuated tilting lever for extrusion. The manually driven extrusion devices are time-proven throughout the world for decades and as such are the current prior art. The extrusion devices are advantageous in that the medical user has a feel for the penetration resistance of the bone cement dough into the bone structures (cancellous bone) by means of the manual force to be expended.

The use of many full-prepacked mixing systems known to date requires the medical user to perform multiple working steps on the devices in a predetermined order, one after the other, until the bone cement dough is ready-mixed and can be applied. Any confusion of the working steps can lead to failure of the mixing device and can therefore cause a disturbance in the surgical procedure. Cost-intensive training of the medical users is therefore required in order to prevent user errors from occurring.

WO 00/35506 A1 proposes a device, in which polymethylmethacrylate cement powder is stored in a cartridge, whereby the cement powder takes up the entire volume of the cartridge and the volume of the intervening spaces between the particles of the cement powder is equal to the volume of the monomer liquid required for the production of bone cement dough with the cement powder stored in the cartridge. The design of the device is appropriate such that the action of a vacuum causes the monomer liquid to be conducted into the cartridge from above, whereby a vacuum is applied to a vacuum connector on the underside of the cartridge for this purpose. As a result, the monomer liquid is aspirated through the cement powder, whereby the air present in the intervening spaces of the cement powder particles is displaced by the monomer liquid. This involves no mechanical mixing of the cement dough thus formed by means of a stirrer.

It is a disadvantage of the system that cement powders, which swell quickly due to the monomer liquid, cannot be mixed with the device, because the rapidly swelling cement powder particles form a gel-like barrier of approximately 1 to 2 cm after ingress of the monomer liquid into the cement powder and impede the migration of the monomer liquid through the entire cement powder. Moreover, conventional cement powders illustrate a phenomenon, which is that the cement powder particles are wetted only poorly by methylmethacrylate due to the difference in surface energies. As a result, the methylmethacrylate penetrates only slowly into the cement powder. Moreover, it cannot be excluded that the monomer liquid, exposed to the action of a vacuum, is aspirated through the vacuum connector after the monomer liquid fully penetrates into the cement powder. In this case, an insufficient amount of monomer liquid for curing by means of radical polymerisation is available and/or the mixing ratio and thus the consistency of the bone cement is changed inadvertently. Moreover, it is a problem that the air trapped between the cement powder particles is to be displaced by the monomer liquid proceeding from top to bottom, because the air, having a lower specific weight than the monomer liquid, tends to migrate upwards in the cement powder rather than downwards in the direction of the vacuum connector under the force of gravity.

From the adhesives and sealant industry, electrically driven extrusion devices are known as well. The devices can be driven both with rechargeable batteries and batteries or by means of a stationary electrical power supply. The devices can extrude particularly thick pasty masses since their extrusion force is very large in some cases. However, it is one disadvantage of the use of electrical motors that these motors contain non-ferrous metals and are expensive purchases. Since the OR area needs to be kept sterile, the devices need to be sterilised with much effort or may even need to be replaced. The presence of electrical wiring may impede the mobility of the user in the OR.

Moreover, pneumatic devices have been proposed as well. The devices require a stationary or mobile compressed air connection (U.S. Pat. No. 2,446,501 A, DE 20 2005 010 206 U1). This necessitates compressed air hoses, which may impede the mobility of the user.

Alternatively, the use of compressed gas cartridges to provide compressed gas is feasible just as well. Devices have been proposed for this purpose, in which the supply of compressed gas is controlled by a valve and, in addition, the flow of the viscous mass is controlled by a second valve (US 2004/0074927 A1, U.S. Pat. No. 6,935,541 B1). These devices have the gas cartridges integrated into the devices. These systems, which are connected to compressed air or contain compressed gas cartridges, always necessitate the presence of a compressed gas source in the absence of which the systems cannot be used.

US 2018/132 917 A1 and US 2018/132 919 A1 proposed full-prepacked mixing systems with a cartridge containing a bone cement powder. A dispensing plunger is provided in the cartridge and a receptacle containing a monomer liquid container is arranged downstream from the cartridge. A conveying plunger is situated on the rear side of the receptacle and can be used to crush the monomer liquid container and to extrude the monomer liquid from the receptacle into the cartridge. In this mixing system, monomer liquid is pressed into compacted cement powder, whereby the cement powder become wetted by the monomer liquid and the air present between the cement powder particles is pressed out by the monomer liquid. This means, a bubble-free cement dough is generated without the action of mechanical mixing devices. For the mixing system to work properly, it is indispensable to connect a separate mechanical extrusion device to the cartridge system. By manual actuation of the extrusion device, the monomer liquid container is opened first, then the monomer liquid is pressed into the cement powder, whereby the cement dough is generated. Subsequently, further actuation of the extrusion device excludes the cement dough thus formed from the cartridge. It is currently customary to use extrusion devices that can be resterilized and need to be cleaned and sterilised after use.

SUMMARY

It is the object of one embodiment to overcome the disadvantages of the prior art. Specifically, it is the object of one embodiment to develop a device that is intended and well-suited for the mixing of the bone cement dough from the starting components, as well as to develop a method for production of a bone cement dough, in particular of a pasty polymethylmethacrylate bone cement dough, whereby the bone cement dough is produced with a device of this type from a cement powder and a monomer liquid, by means of which the drawbacks of the previous devices and methods are overcome. It is the object of one embodiment to improve a device like the ones according to US 2018/132 917 A1 and US 2018/132 919 A1 such that an amount of monomer liquid that can be predetermined can be pressed into the cement powder, if at all possible without trapping gas or air. Accordingly, what is to be attained with the device according to one embodiment and the method according to one embodiment is that a homogeneous bone cement dough can be generated and applied throughout the entire extrusion process even with the device being very simple and inexpensive in design and the device also being very easy and simple to use.

It shall be feasible to drive the device without an extrusion device, and the device is to be as easy as possible to operate. The design is to be inexpensive to allow the device to be used just a single time for hygienic reasons. As many as possible or all of the processes taking place in the device, such as the mixing of the starting components, the dispensing of the bone cement dough, and, if applicable, the opening of the monomer liquid container and, if applicable, the opening of the cartridge, are to take place in the smallest possible number of working steps and are to be automated to the extent possible and in one embodiment are to be driven by a single linear drive only.

Accordingly, the development of a device for the mixing of cement powder and monomer liquid is also the object of one embodiment. The handling of the device is to be maximally simplified in order to basically prevent operating errors resulting from installation steps taking place incorrectly. It should be feasible for the medical user to actuate the device directly after removing it from a packaging. Assembly and working steps are to be omitted due to the design of the device. It shall be possible to store cement powder and monomer liquid separate from each other in the device. The device is preferred to be a full-prepacked mixing system. It shall be feasible to mix the two cement components within few seconds in the closed device without any manual mixing with mixing wheels and/or mixing vanes being required. In this context, the mixing is to be appropriate such that the medical user does not contact the cement powder and the monomer liquid. Moreover, the mixing system shall be appropriate such that no assembly steps and no external vacuum are required for monomer transfer. The mixing system to be developed shall allow the cement dough produced after the two cement components have been mixed to be extruded without connecting an external extrusion device, in one embodiment through manual actuation of the device itself. The device shall allow polymethylmethacrylate bone cement dough to be prepared and applied without requiring any additional equipment, such as vacuum sources, vacuum hoses, and extrusion devices. Moreover, the monomer liquid shall be transferred appropriately such that only monomer liquid with no gas inclusions and/or air bubbles rather than a mixture of air and monomer liquid is transferred into the cement powder. This shall prevent a formation of air inclusions in the bone cement dough.

In one embodiment, the device is to also ensure the secure storage of cement powder and monomer liquid in separate compartments such that any inadvertent mixing of the cement components during storage of the device is excluded. The device is to allow for sterilisation with ethylene oxide gas. For this purpose, the cement powder stored in the device must be accessible to ethylene oxide.

The objects of one embodiment are met by a device for production of a bone cement dough from a monomer liquid and a cement powder as starting components of the bone cement dough, and for dispensing of the bone cement dough, the device comprising A) a cartridge with a cylindrical internal space;

B) a cartridge head with a dispensing opening for dispensing the bone cement dough, whereby the cartridge head closes the cartridge on a front side of the cartridge except for the dispensing opening;

C) a conveying plunger that is arranged in the internal space of the cartridge and is stored in the internal space of the cartridge such that it is pushable in the direction of the dispensing opening;

D) a dispensing plunger that is arranged in the internal space of the cartridge between the dispensing opening and the conveying plunger and that is supported in the internal space of the cartridge such that it is pushable in the direction of the dispensing opening, whereby a rear side of the dispensing plunger facing the conveying plunger comprises a depression that tapers in the direction of the cartridge head;

E) a first hollow space that is bordered by the cartridge head, by internal walls of the cartridge, and by the dispensing plunger, whereby the cement powder is arranged in the first hollow space;

F) a second hollow space that is part of the cylindrical internal space of the cartridge, whereby the second hollow space is bordered by the dispensing plunger and the conveying plunger;

G) a rear-side part of the internal space of the cartridge, whose front side is bordered by a rear side of the conveying plunger that faces away from the dispensing plunger;

H) a conducting means, which connects the second hollow space to the rear-side part of the internal space of the cartridge, by-passing the conveying plunger, such as to be permeable to the monomer liquid, whereby the conducting means can be closed by the conveying plunger with respect to the second hollow space through a shift of the conveying plunger in the direction of the dispensing plunger; and I) a feedthrough, whereby the feedthrough commences at a tip of the tapering depression, extends through the dispensing plunger and connects the first hollow space and the second hollow space such as to be permeable to the monomer liquid, but impermeable to the cement powder.

BRIEF DESCRIPTION OF DRAWINGS

The accompanying drawings are included to provide a further understanding of embodiments and are incorporated in and constitute a part of this specification. The drawings illustrate embodiments and together with the description serve to explain principles of embodiments.

Other embodiments and many of the intended advantages of embodiments will be readily appreciated as they become better understood by reference to the following detailed description. The elements of the drawings are not necessarily to scale relative to each other. Like reference numerals designate corresponding similar parts.

Figure 1:
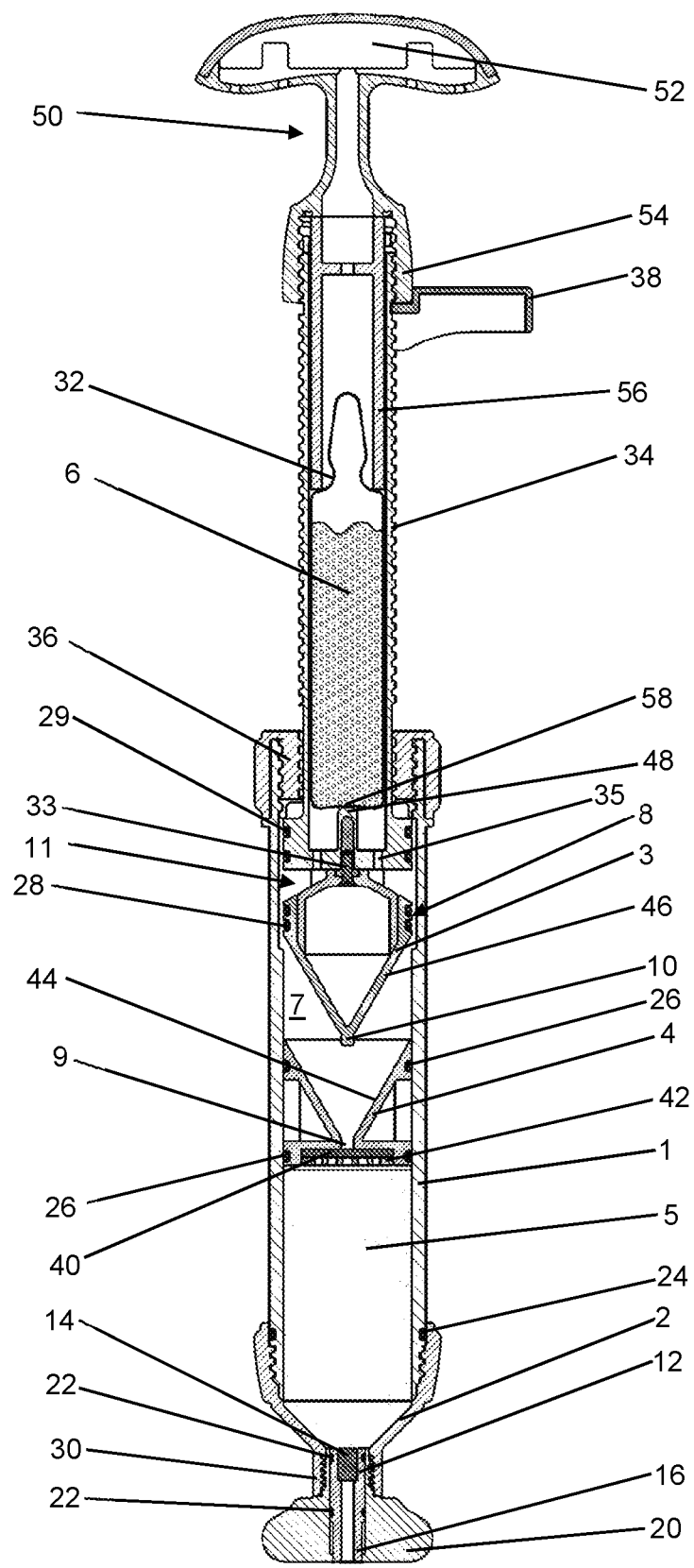
Figure 2:
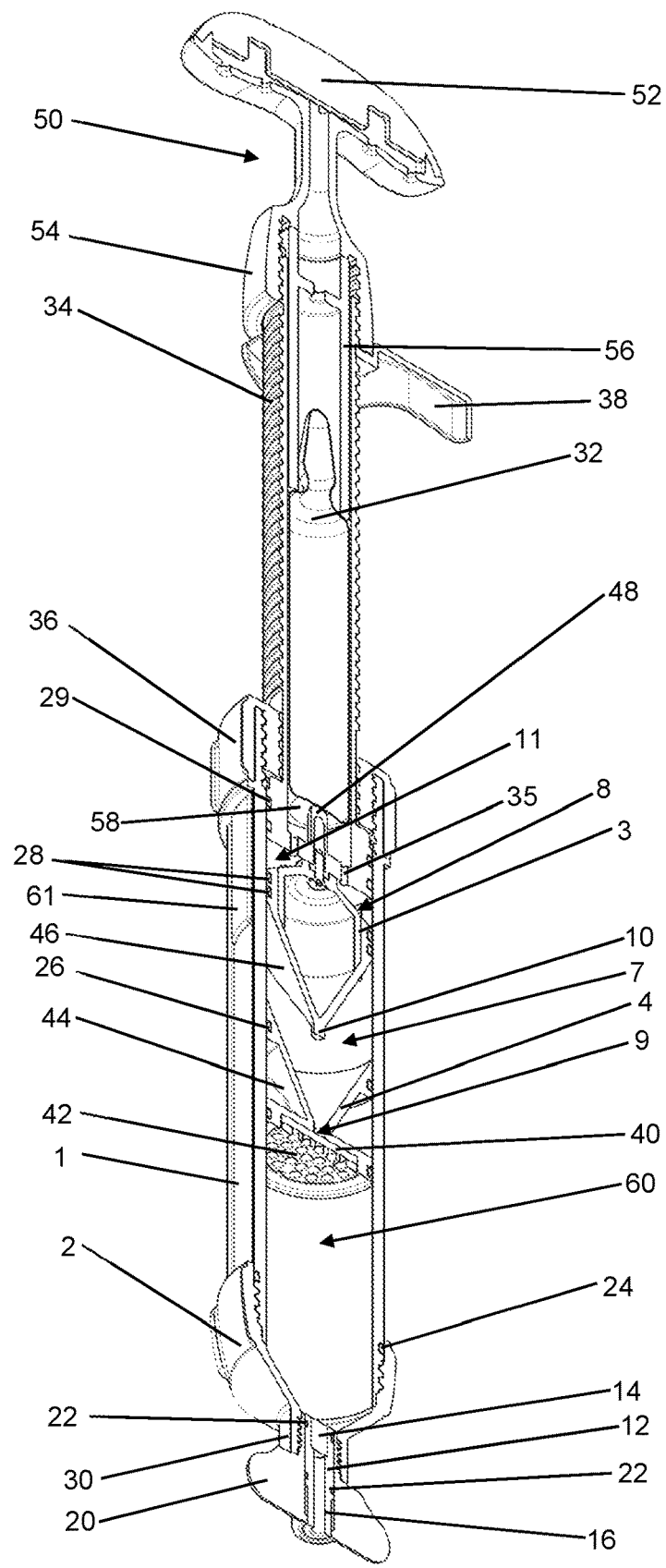
Figure 3:
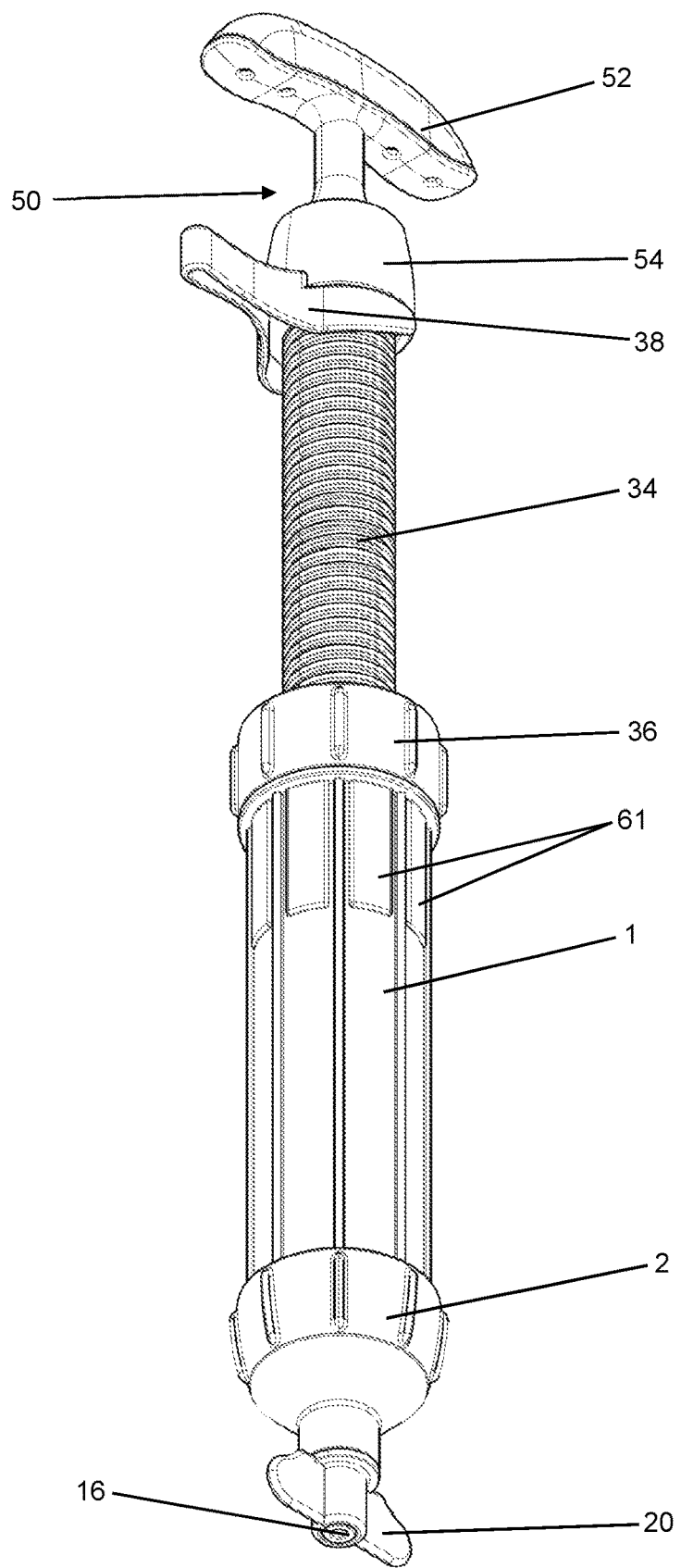
Figure 4:
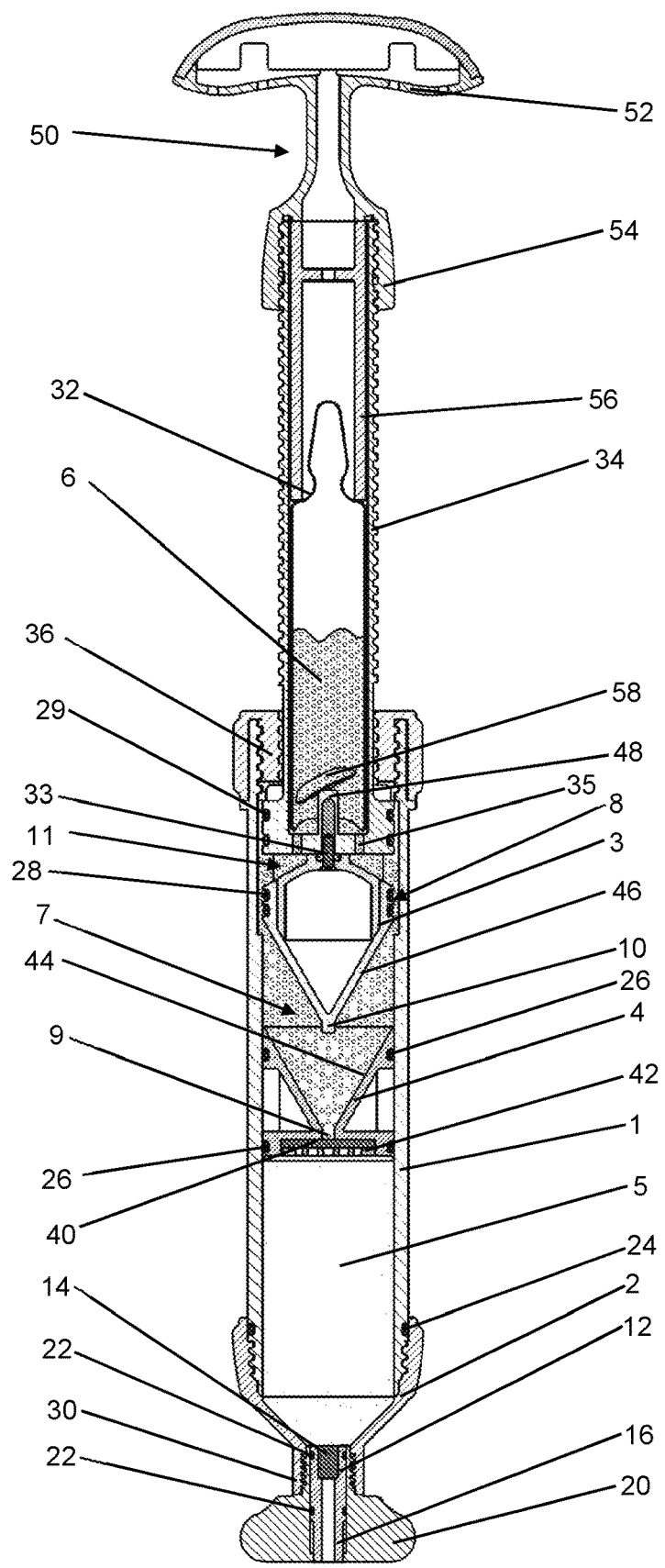
Figure 5:
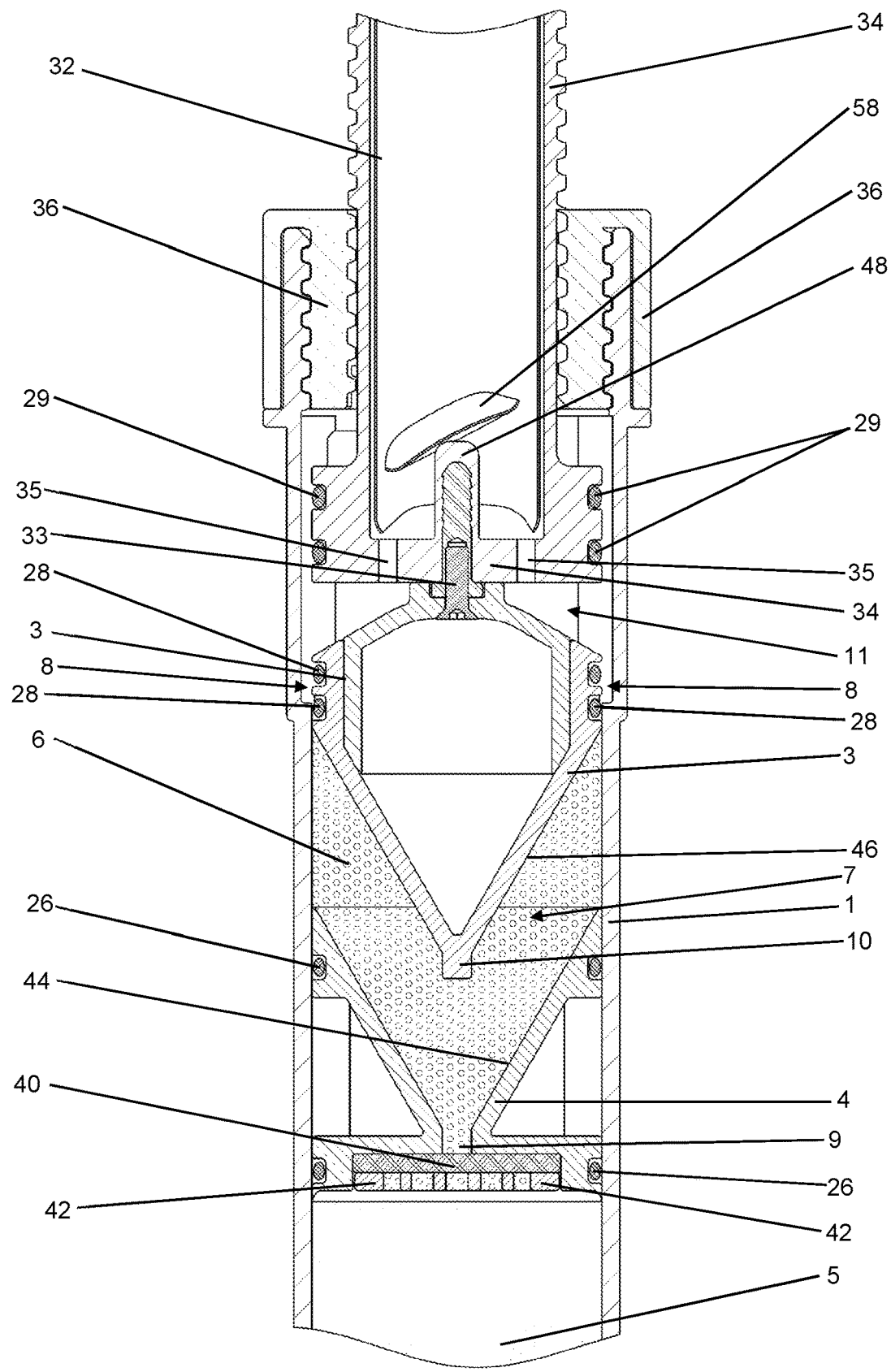
Figure 6:
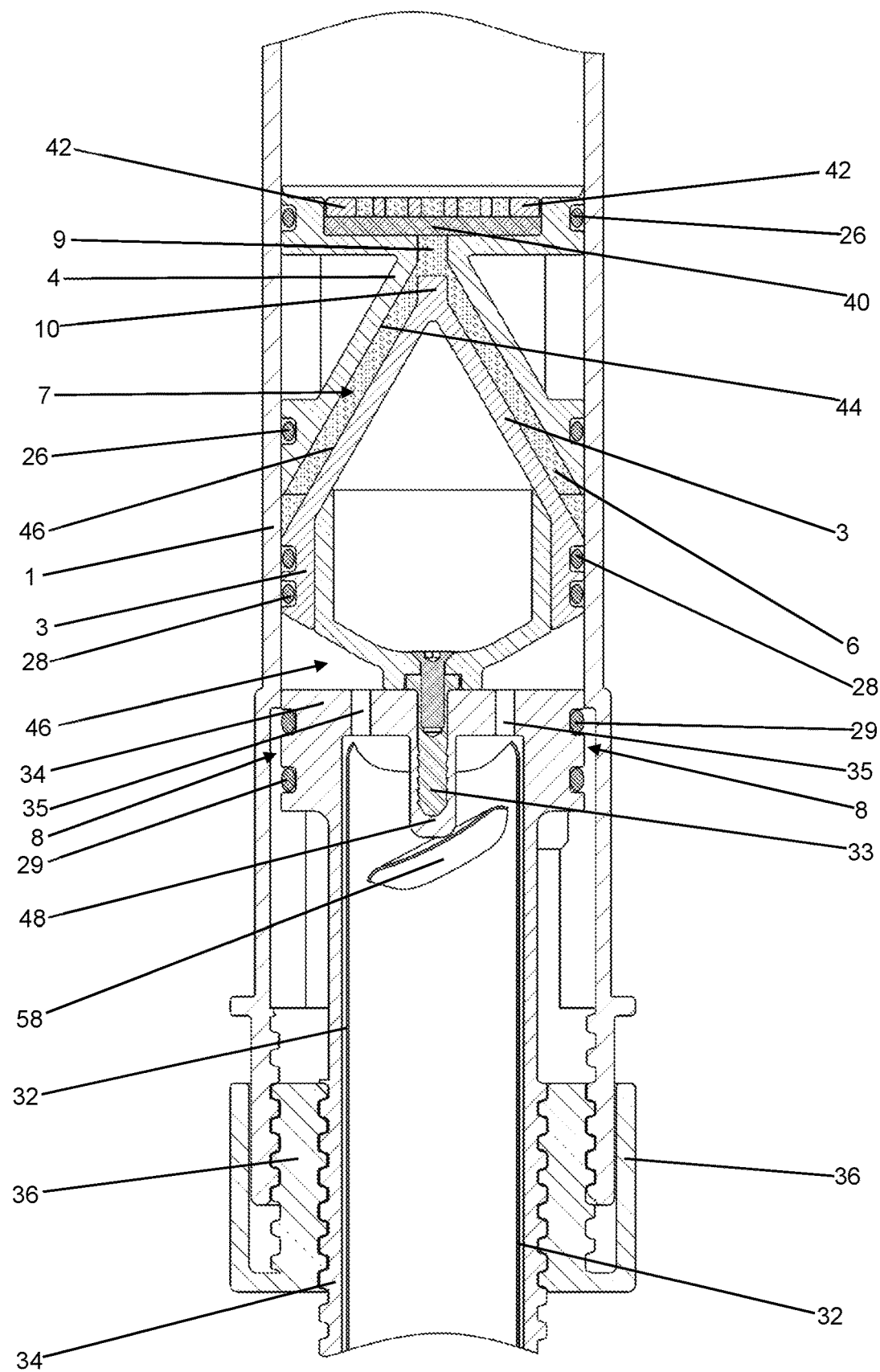
Figure 7:
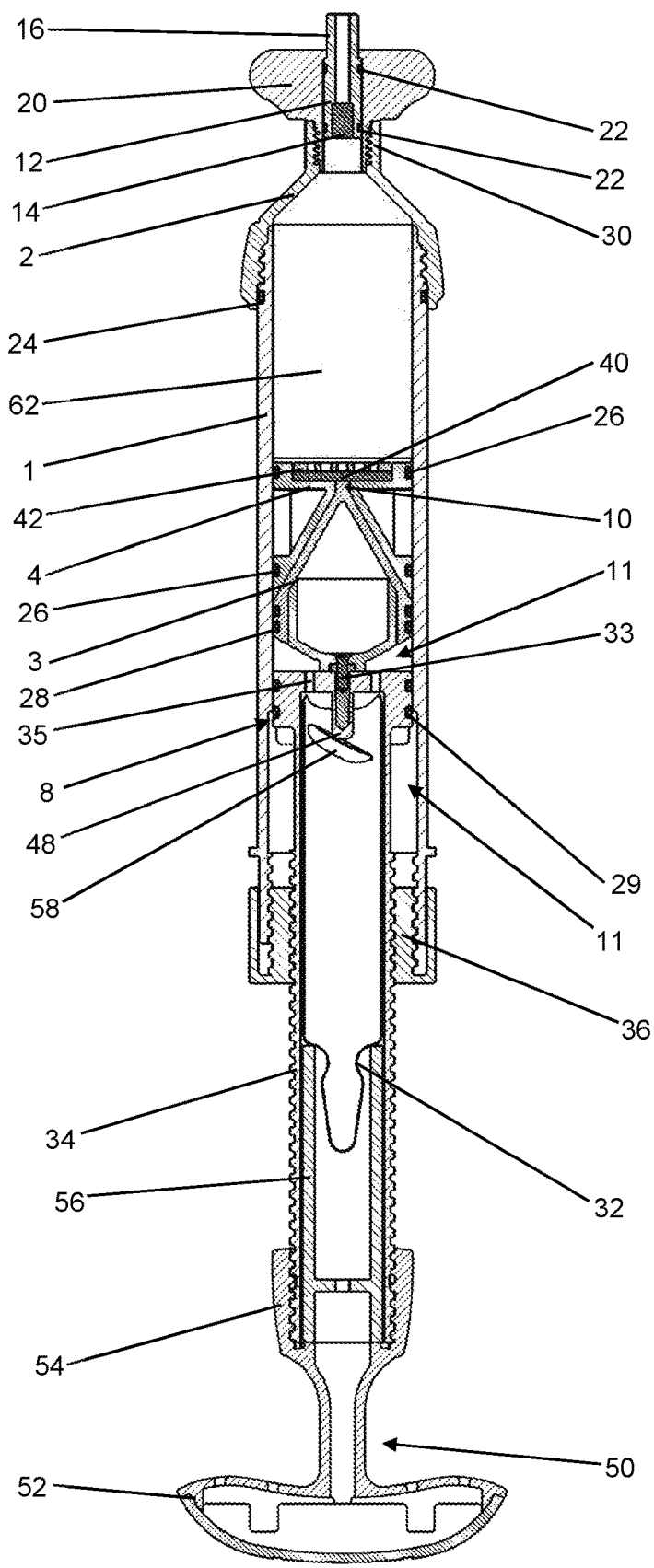
Figure 8:
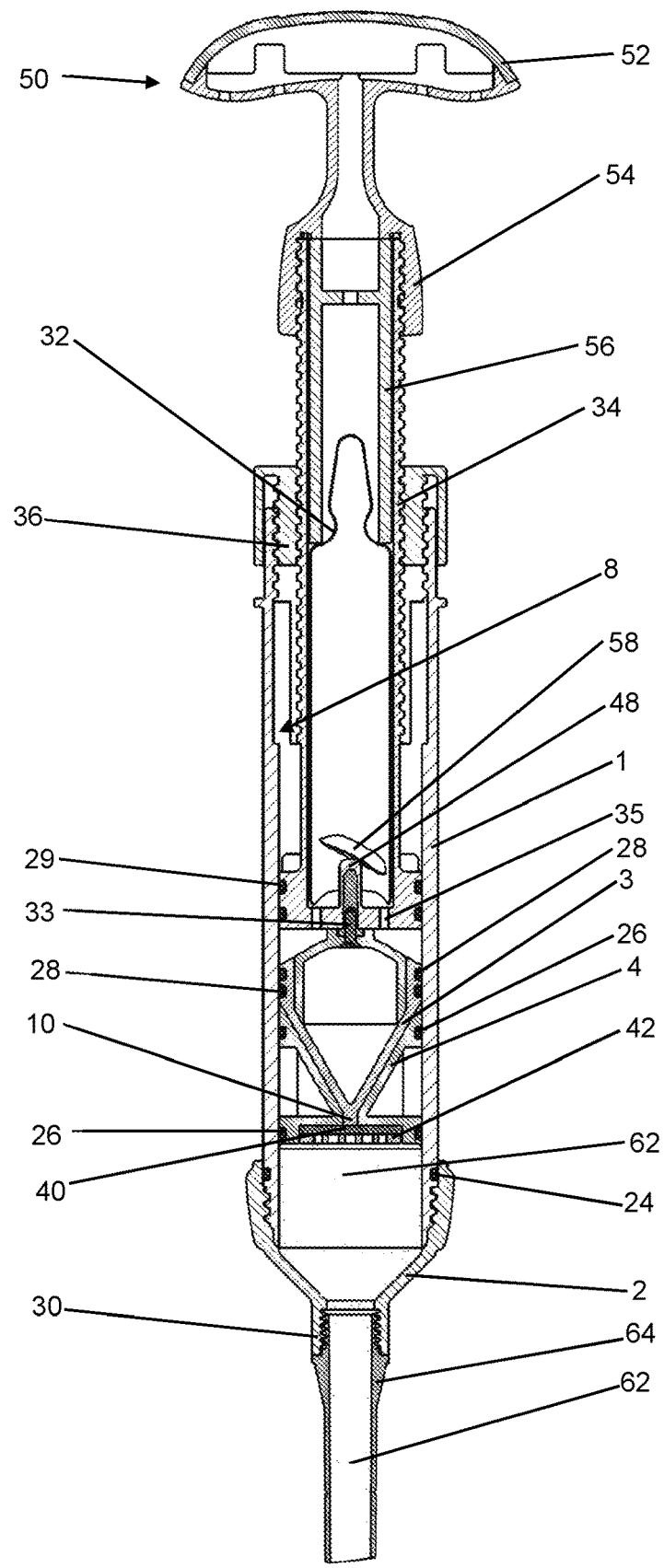
Figure 9:
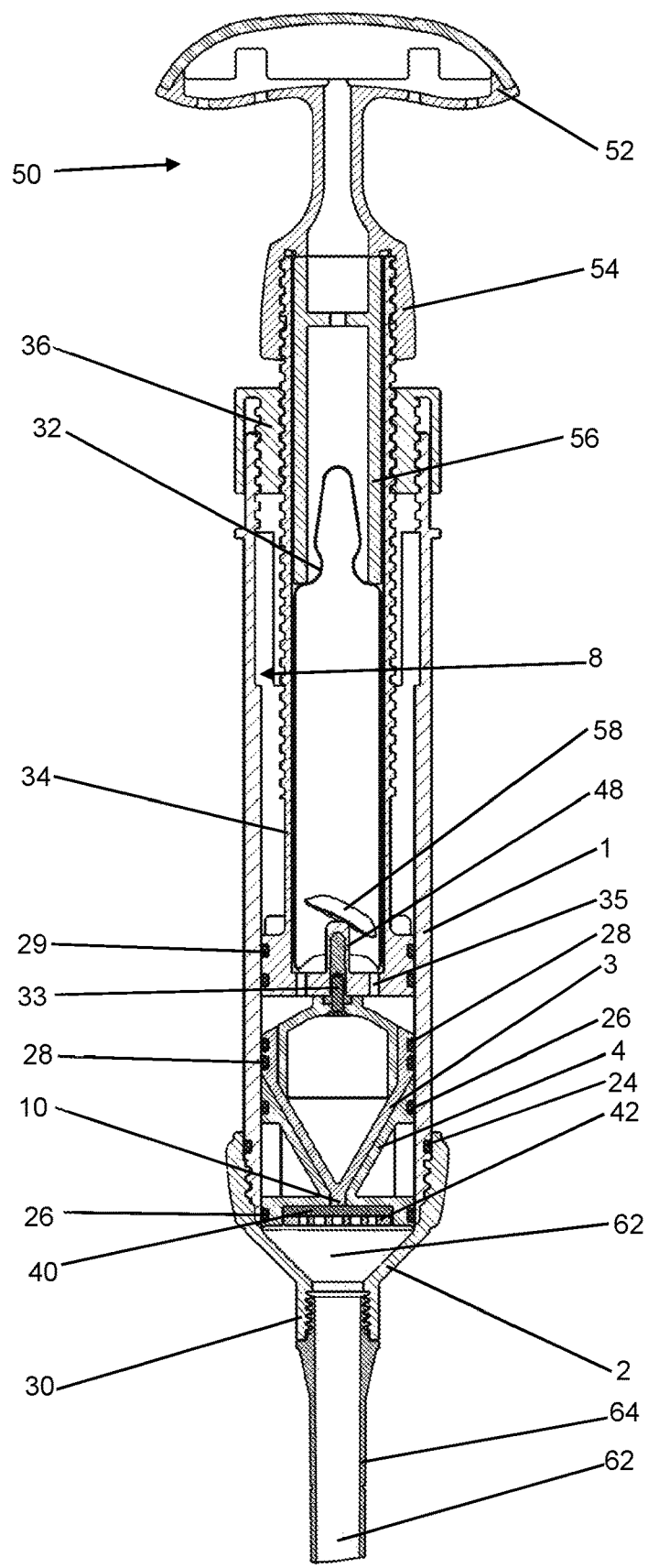

Further exemplary embodiments shall be illustrated in the following on the basis of nine schematic figures, though without limiting the scope of the embodiments. In the figures:

FIG. 1: illustrates a schematic cross-sectional view of an exemplary device according to one embodiment for storage and mixing of a monomer liquid and a cement powder in a starting state and/or storage state of the device;

FIG. 2: illustrates a schematic perspective cross-sectional view of the device according to FIG. 1 without the monomer liquid and the cement powder;

FIG. 3: illustrates a schematic perspective external view of the device according to FIGS. 1 and 2;

FIG. 4: illustrates a schematic cross-sectional view of the device according to FIGS. 1 to 3 with an opened monomer liquid container in it;

FIG. 5: illustrates a schematic cross-sectional view of a detail magnification of the device according to FIGS. 1 to 4 shortly after the conducting means is closed; and FIG. 6: illustrates a schematic cross-sectional view of a detail magnification of the device according to FIGS. 1 to 5 while the monomer liquid is being pressed into the cement powder, whereby the device was rotated with the cartridge head upwards; and FIG. 7: illustrates a schematic cross-sectional view of the device according to FIGS. 1 to 6 with the stopper pushed forward and marker means as an indicator of the bone cement dough being ready for use;

FIG. 8: illustrates a schematic cross-sectional view of the device according to FIGS. 1 to 7 during the dispensation of the bone cement dough; and FIG. 9: illustrates a schematic cross-sectional view of the device according to FIGS. 1 to 8 after the dispensation of the bone cement dough;

DETAILED DESCRIPTION

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

One embodiment can provide the conducting means to be at least one groove or at least one bypass line. The at least one groove can in one embodiment be arranged in the internal wall of the cartridge. Also in one embodiment, the at least one groove can extend in axial direction of the internal space along a part of the internal space. The at least one groove or the at least one bypass line can allow the monomer liquid to be conducted into the second hollow space while bypassing the conveying plunger.

According to one embodiment, due to the easier manufacture, the at least one groove is preferred as conducting means over at least one bypass line or other conducting means.

One embodiment can provide the conducting means, in particular the at least one groove or the at least one bypass line, to be arranged in a region in the direction of the rear side of the cartridge.

One embodiment can provide the conducting means, in particular the at least one groove, to extend in axial direction of the internal space along a part of the internal space.

The conducting means, in particular the at least one groove, extending in axial direction of the internal space along a part of the internal space does not necessarily mean that the conducting means, in particular the at least one groove, extends parallel to the axial direction of the internal space, but rather that it does not extend perpendicular to the axial direction of the internal space unless a corresponding groove were wide enough to allow a transfer of monomer liquid into the second hollow space bypassing the conveying plunger to proceed. The conducting means, in particular the at least one groove, can be linear or curved in this context. However, according to one embodiment, the conducting means, in particular in the at least one groove, is preferred in one embodiment to extend parallel to the axial direction of the internal space, since the cartridge with the conducting means, in particular the at least one groove, is then somewhat easier to design and manufacture.

A single, ring-shaped, but sufficiently wide groove is disadvantageous in that the conveying plunger travelling over the groove does not have any grip, unless guide struts are present that bridge the groove and guide the conveying plunger at its radial circumference when it travels over the groove.

One embodiment can just as well provide multiple grooves or a multitude of grooves to be used as the at least one groove. The design effort for this purpose is not very high and the transfer of monomer liquid is improved by the larger total cross-sectional area.

In particular, the conducting means can be closable in liquid-tight manner through a shift of the conveying plunger in the direction of the dispensing plunger from the conveying plunger against the second hollow space.

The conducting means connecting the second hollow space to the rear-site part of the internal space of the cartridge by bypassing the conveying plunger in one embodiment means that the axial extension from the beginning to the end of the conducting means has a greater distance than the axial extension of the part of the conveying plunger that touches against the internal space of the cartridge, in particular than the axial extension of the part of the conveying plunger that is intended for closing the conducting means.

It shall be noted expressly that the bone cement dough can be dispensed from the device onto a spatula or into a vessel for later use. Direct application on a patient is therefore neither required nor claimed.

When the conveying plunger is being pushed in the direction of the dispensing plunger and thus crosses and closes the conducting means, in particular the at least one groove or the at least one bypass line, the second hollow space can progressively decrease in size.

In one embodiment, the device is also designed for storage of the cement powder and particularly in one embodiment for storage of the monomer liquid as well.

One embodiment can provide a dispensing tube to be attachable to the front side of the cartridge, in particular to the cartridge head, whereby the dispensing tube particularly in one embodiment borders the dispensing opening.

One embodiment can provide the internal space of the cartridge to be bordered by an internal wall of the cartridge.

The conveying plunger can be cambered on its side that is opposite from the dispensing plunger.

One embodiment can provide the volume of the second hollow space to be at least equal to the volume of the monomer liquid used here, in particular to the volume of the monomer liquid in a monomer liquid container of the device. In one embodiment, the volume of the second hollow space is larger by at least one third than the volume of the monomer liquid used here, in particular the volume of the monomer liquid in a monomer liquid container of the device.

The internal space of the cartridge has a cylindrical geometry except for the asymmetries caused by the conducting means, in particular except for the at least one groove or the merging sites to the at least one bypass line. The cylindrical shape is the simplest shape by means of which the internal space of the cartridge can be implemented. A cylindrical shape shall be understood geometrically to mean the shape of a general cylinder of any footprint, i.e. not just a cylinder having a circular footprint. Accordingly, the internal wall of the internal space of the cartridge can be realized by means of the cylinder jacket of a cylinder of any footprint, in particular of different footprints, including non-circular or non-round footprints. However, according to one embodiment, a cylindrical geometry with a rotationally symmetrical and, in particular, circular footprint is preferred for the internal space, since these are the easiest to manufacture.

One embodiment can provide a front side of the conveying plunger that faces the dispensing plunger to include a surface that projects in the direction of the dispensing plunger and is preferred to taper steadily in the direction of the dispensing plunger.

As a result, gas or air inclusions can easily escape through the conducting means, and particularly through the at least one groove, when the device is held with the cartridge head down while the monomer liquid is conducted from the rear-side part of the internal space of the cartridge into the second hollow space.

One embodiment can provide the depression that tapers in the direction of the cartridge head to be a depression in the form of a funnel-shaped surface that tapers steadily originating from the internal wall of the cartridge, whereby a projecting surface on the front side of the conveying plunger can in one embodiment be inserted into the funnel-shaped surface on the rear side of the dispensing plunger, whereby the feedthrough in the dispensing plunger particularly in one embodiment merges into the dispensing plunger at the lowest site of the funnel-shaped surface.

By this means, it can be assured that a large fraction of a monomer liquid that is present between the conveying plunger and the dispensing plunger is pushable from the second hollow space into the first hollow space and that air inclusions or gas inclusions can be transferred, in particular pushed, easily from the second hollow space into the first hollow space.

Particularly in one embodiment, the funnel-shaped depression at the rear side of the dispensing plunger is a negative form of the projecting surface on the front side of the conveying plunger.

According to a preferred development, one embodiment can provide a front side of the conveying plunger that faces the dispensing plunger and the rear side of the dispensing plunger facing the conveying plunger to be shaped with matching surfaces with respect to each other such that the front side of the conveying plunger touches against the rear side of the dispensing plunger with matching surfaces, when the conveying plunger is pushed against the dispensing plunger, whereby preferably in one embodiment the volume of the second hollow space thereby is reducible to a maximum of 1% of the volume of the second hollow space in a starting state.

As a result, all or a large fraction of a monomer liquid conducted into the second hollow space can be pressed into the first hollow space by pushing the conveying plunger in the direction of the dispensing plunger while the conveying means is already closed.

Moreover, one embodiment can provide the rear side of the dispensing plunger that faces the conveying plunger to include a funnel-shaped surface as the tapering depression that has the feedthrough arranged in its lowest site, and a front side of the conveying plunger that faces the dispensing plunger to include a projecting cone-shaped surface with the same slope as the funnel-shaped surface on the rear side of the dispensing plunger, whereby a cylindrical pin that can be inserted into a cylindrical depression as part of the feedthrough in the dispensing plunger is preferred to be arranged on the tip of the projecting cone-shaped surface on the front side of the conveying plunger.

By this means, not only can the retention of gas or air inclusions in the second hollow space be prevented, but gas or air inclusions can easily escape through the feedthrough while the monomer liquid is filled into the second hollow space. Expelling gas inclusions and/or air inclusions from between the powder particles of the cement powder allows a bone cement dough to be produced that is free or depleted of bubbles. Moreover, all or most of the monomer liquid contained in the second hollow space can be transferred to the first hollow space.

In this context, one embodiment can provide the funnel-shaped surface on the rear side of the dispensing plunger and the projecting cone-shaped surface on the front side of the conveying plunger to have the same base diameter.

In this context, one embodiment can provide the funnel-shaped surface on the rear side of the dispensing plunger to include an angle of slope of at least 45°, in one embodiment of at least 55°, in one embodiment of at least 60°, and the cone-shaped surface on the front side of the conveying plunger to include a matching angle of slope of at least 45°, in one embodiment of at least 55°, in one embodiment of at least 60°.

This enables the rapid escape of gas inclusions from the second hollow space into the first hollow space when the device is set up vertically with the cartridge head downwards.

One embodiment can provide the dispensing plunger and/or the conveying plunger to be sealed with respect to an internal wall of the cartridge, whereby the internal wall of the cartridge is a boundary of the internal space of the cartridge. In this context, one embodiment can provide the dispensing plunger and/or the conveying plunger to be sealed with respect to the internal wall of the cartridge by at least one sealing ring. In this context, one embodiment can, in turn, particularly in one embodiment provide the at least one sealing ring to be arranged in at least one circumferential groove in the dispensing plunger and/or conveying plunger.

The sealing prevents the monomer liquid from possibly being pushed such as to bypass the dispensing plunger and/or the conveying plunger and from thus having an adverse influence on the desired mixing ratio or causing contamination of the surroundings.

One embodiment can provide a container to be arranged on the rear side of the conveying plunger, with a monomer liquid container containing the monomer liquid being arranged in the container, in particular an ampoule made of glass or plastics, whereby the monomer liquid container is openable inside the container and whereby the container is connected to the rear-side part of the internal space of the cartridge in fluid-permeable manner via at least one monomer line, whereby an opening means is in one embodiment arranged on a side of the container opposite from the conveying plunger, by means of which the monomer liquid container is openable inside the container, whereby the opening means is preferred in one embodiment to be a sleeve attached to a cap, whereby the cap can be screwed onto a thread of the container and the cap includes a counter-thread for this purpose such that, when the cap is being screwed on, the monomer liquid container, in particular the ampoule, is pushed, by the sleeve, onto at least one projecting pin on the internal side of the container and thus the monomer liquid container, in particular the ampoule, is breakable open.

By this means, a full-prepacked mixing system is provided, in which all starting components of the bone cement dough, namely the monomer liquid and the cement powder, can be stored and mixed in the device. The handling of the monomer liquid can thus take place inside the device and the user is protected from the cement powder and, in particular, from the monomer liquid.

One embodiment can provide the container to be attached to the conveying plunger.

By this means, a joint motion of the conveying plunger and container can be synchronised. Moreover, a more stable motion of the conveying plunger can be attained. In this context, the conveying plunger can be supported against the container such that it can be rotated axially, whereby the rotary axis coincides with the axis of the cylindrical internal space of the cartridge. By this means, the conveying plunger can move linearly and without rotation in the internal space of the cartridge when the container is being screwed in.

A detachable locking element can be provided that prevents the opening means from being operated In one embodiment, the monomer liquid container is plugged into a fit in the container such that the monomer liquid container is being held in the container. A screen or a filter for retention of fragments of the monomer liquid container can be arranged at the merging site to the at least one monomer line.

The sleeve can be a piece of tubing. The sleeve can push onto the shoulders of an ampoule as monomer liquid container such that the ampoule is pushed open on an ampoule base of the ampoule in the container. In one embodiment, the sleeve and the cap are a single part or form a unit.

In one embodiment, glass ampoules, plastic ampoules, plastic bags, film bags, plastic compound bags, and aluminium-plastic compound bags that are suitable for storing monomer liquid can be used as monomer liquid container.

Moreover, one embodiment can just as well provide a ventilation opening connecting the internal space of the container to the surroundings to be arranged in the wall of the container or in the opening means.

By this means, the internal space of the container can easily be evacuated and sterilised with a sterilising gas.

A preferred embodiment can just as well provide the at least one ventilation opening to be arranged so close in the vicinity of a screw cap, in particular of a screw cap as opening means for opening a monomer liquid container, in the container such that the at least one ventilation opening is closed through a motion of the screw cap in the direction of the cartridge before a monomer liquid container that contains the monomer liquid and is arranged in the container is being opened through the motion of the screw cap.

By this means, the monomer liquid cannot exit from the internal space of the container, when the at least one ventilation opening is closed by the screw cap moving in the direction of the cartridge before the monomer liquid container is opened through the motion of the screw cap, i.e. for example is squashed, splintered, punctured or torn open in the internal space of the container.

The container can include a cylindrical internal space that is suitable for accommodation of an ampoule as monomer liquid container with a cylindrical external circumference. The container can then be called an ampoule holder, in particular if the internal diameter of the internal space of the container matches the external diameter of the ampoule to be inserted.

The internal space of the container can have a projection for fracturing, puncturing or cutting open the monomer liquid container arranged in it, whereby the projection, in particular, is a puncture mandrel or puncturing mandrel. The projection is in one embodiment situated in a merging site of the internal space of the container with respect to the at least one monomer line.

In devices according to one embodiment having a container, one embodiment can just as well provide the container to include an external thread that can be screwed into an internal thread on an end of the cartridge opposite from the cartridge head, whereby the conveying plunger is pushable in the direction of the dispensing opening by screwing the container into the cartridge and the dispensing plunger is pushable by the conveying plunger in the direction of the dispensing opening, whereby the internal thread in one embodiment is part of a ring sleeve that is connected to the cartridge on the end of the cartridge opposite from the cartridge head.

By this means, the device can be operated from outside through a screw motion. The screw motion is advantageous in ne embodiment in that a forceful propulsion of the conveying plunger and dispensing plunger is enabled such that even viscous bone cement doughs can be extruded from the cartridge with the device.

Moreover, one embodiment can provide the external side of the container to possess no external thread in a first section that originates from a front side that faces the cartridge head, and to possess an external thread in a second section.

By this means, the conducting means can initially be closed by advancing the container and thus the conveying plunger into the internal space of the cartridge, before the external thread of the conveying plunger engages the internal thread of the cartridge. Since the two steps are chronologically separate, an operating error of the device can be prevented easily.

Moreover, one embodiment can provide the conducting means to terminate or merge at a site on the internal wall of the cartridge that is situated at an appropriate axial distance from the dispensing plunger relative to the axis of the cylindrical internal space, such that the volume of the second hollow space is at least equal to the volume of the monomer liquid conducted into it through the conducting means, in particular of the monomer liquid contained in the monomer liquid container, when the conveying plunger is pushed just far enough in the direction of the dispensing plunger such that the conveying plunger closes the conducting means with respect to the second hollow space.

By this means, all of the monomer liquid can be conducted into the second hollow space and gases can exit from the second hollow space such that the second hollow space contains only the monomer liquid when the closure means closes the conducting means.

Moreover, one embodiment can just as well provide a stopper to be arranged in the dispensing opening, with the stopper closing the dispensing opening impermeable to the cement powder, in particular closing the dispensing opening permeable to gases, whereby the stopper in one embodiment is arranged in the dispensing opening such as to be mobile such that the stopper is pushable out of the dispensing opening by pressing on the ready-mixed bone cement dough, whereby it is preferred to one embodiment to have a marker means that is visible from outside attached to the stopper, whose position can be read from outside to indicate whether the stopper is pushed outward in the dispensing opening.

By this means, premature leakage of the bone cement dough can be prevented. One embodiment allows it to be recognized from outside when the bone cement dough is ready-mixed up to the dispensing opening. This is the result of the bone cement dough being flowable, while the cement powder is not flowable, such that the stopper is moved only if the bone cement dough is ready-mixed or if the cement powder is at least completely wetted and the dispensing plunger exerts a pressure on the stopper via the bone cement dough.

The stopper can be part of a closure system closing the dispensing opening. In this context, the stopper can be arranged in a cylindrical borehole of the closure system such as to be mobile in axial direction. The closure system can be screwed into an internal thread on a socket of the cartridge head by means of an external thread. Obviously, the closure system can alternatively just as well include a cap with an internal thread that is screwed onto a socket on the cartridge head with an external thread. After removing the closure system, the socket can be connected to a dispensing tube.

The cartridge is preferred to be hollow cylinder-shaped. The cartridge head can be conical in shape. This allows a gas to exit from the cartridge head more easily. Moreover, a dead volume remains inside the cartridge head, when the dispensing plunger is pushed up to the cartridge head. Less well-mixed fractions of the bone cement dough that cannot be dispensed can be retained in this place.

The feedthrough is in one embodiment arranged on the tip or in the envelope of a cone of a cone-shaped depression on the rear side of the dispensing plunger.

One embodiment can just as well provide the volume of the monomer liquid used here, in particular the volume of the monomer liquid contained in the monomer liquid container, to be at least at most equal to the volume of the second hollow space.

One embodiment can provide the cement powder to be appropriately compacted in the first hollow space such that the cement powder particles are not freely mobile. This ensures that the monomer liquid can spread rapidly and homogeneously in the cement powder due to capillary forces.

One embodiment can provide a detachable locking means preventing a motion of the conveying plunger against the cartridge to be connected to the conveying plunger. In one embodiment, the locking means is arranged on the container for the monomer liquid container and blocks the container from being pushed or screwed into the cartridge and thus blocks a motion of the conveying plunger in the cartridge.

The cartridge is in one embodiment manufactured from a thermoplastic material, in particular with an injection molding procedure. It is preferred to one embodiment for the other parts of the device, such as the dispensing plunger, the conveying plunger, and the cartridge head, as well as, if applicable, the container and the stopper, to also be manufactured from a thermoplastic material, in particular with an injection molding procedure.

Moreover, one embodiment can provide the feedthrough to be closed by a stopper that is impermeable to gases and liquids, whereby the stopper is shiftable in the feedthrough in the direction of the cartridge head, whereby the front side of the conveying plunger in one embodiment has a pin arranged on it by means of which the stopper in the feedthrough is pushable out of the feedthrough and thus the feedthrough is openable, whereby, particularly in one embodiment, the pin has an appropriate axial extension with respect to the cylindrical internal space such that, upon the pin and the stopper touching, the volume between the rear side of the dispensing plunger and the front side of the conveying plunger in the internal space of the cartridge it is at least equal to the volume of the monomer liquid in a monomer liquid container that is arranged or is to be arranged in the device.

By this means, the monomer liquid cannot penetrate into the first hollow space prematurely such that it does not swell up with the cement powder and form a gel like barrier that can counteract the further spreading of the monomer liquid in the cement powder.

The underlying objects of the present embodiments are also met by a method for the production of a bone cement dough, in particular a pasty polymethylmethacrylate bone cement dough, whereby the bone cement dough is produced from a cement powder and a monomer liquid with a device according to one embodiment as described above, characterized by the following steps proceeding in the order given:

A) conducting the monomer liquid through the conducting means into the second hollow space;

B) pushing the conveying plunger in the direction of the dispensing plunger until the dispensing plunger closes all connections of the conducting means to the second hollow space;

C) holding the device with the cartridge head upwards and pushing the conveying plunger further in the direction of the dispensing plunger, whereby air or gas is removed from the first hollow space and from the second hollow space through the cartridge head, and whereby the monomer liquid is pushed from the second hollow space into the cement powder in the first hollow space;

D) the conveying plunger pushing the dispensing plunger in the direction of the dispensing opening, whereby the bone cement dough produced in the first hollow space flows out through the dispensing opening.

One embodiment, can provide no treatment of a human or animal body to take place in the method according to one embodiment, in particular no treatment of a human or animal body that is excluded from patenting to take place.

Moreover, one embodiment can provide for the bone cement dough to be produced in the first hollow space during step C) and/or after step C), but before step D).

One embodiment can just as well provide the device to be set up or held with the cartridge head downwards in step A), and in one embodiment in step B) as well, and, in step C), gas inclusions to escape from the second hollow space through the feedthrough, the first hollow space, and the dispensing opening in the cartridge head, in one embodiment to escape through a filter in the dispensing opening that is permeable to gases, but impermeable to the cement powder, whereby the filter closes the dispensing opening permeable for gases and impermeable for the cement powder.

By this means, an exactly predetermined amount of the monomer liquid can be introduced into the cement powder. Moreover, a bone cement dough that is free or depleted of bubbles can be produced by this means.

Moreover, one embodiment can provide the conveying plunger to touch against the dispensing plunger with matching surfaces in step D), and in one embodiment in step C), the volume of the second hollow space to be reduced completely to zero or down to a maximum of 1% of the volume of the second hollow space in a starting state.

By this means, the monomer liquid can be pressed completely from the second hollow space into the cement powder in the second hollow space.

Moreover, one embodiment can provide the pressure acting on the bone cement dough in step D) to move or push forward a stopper in the dispensing opening, whereby the stopper is in one embodiment removed from the dispensing opening subsequently and, particularly in one embodiment, then an application tube is attached to the cartridge head of the cartridge.

This allows a user of the device to recognise when the bone cement dough is ready for use.

One embodiment can just as well provide for a monomer liquid container containing the monomer liquid to be opened in a container before step A) and the monomer liquid to be released in the container, whereby the container is arranged on, specifically is attached to, a rear side of the conveying plunger that faces away from the dispensing plunger, and the monomer liquid flows from the container through the conducting means into the second hollow space in step A), whereby, in one embodiment, the conveying plunger in steps B) and C) and the conveying plunger and the dispensing plunger in step D) are driven by the container being pushed or screwed into the cartridge.

This allows the method to be implemented easily by hand. The device can be used as full-prepacked mixing system and any contact of the user with the monomer liquid during the method can be excluded.

One embodiment is based on finding, surprisingly, that having a conducting means in the wall of the cartridge that can be closed by a dispensing plunger allows a hollow space (the second hollow space presently) to be closed with respect to the outside or with respect to a rear part of an internal space of the cartridge through a motion of the conveying plunger into the internal space of the cartridge and thus to provide a monomer liquid reservoir that is closed towards the outside, but is connected in the direction of a (first) hollow space containing the cement powder such as to be permeable to the monomer liquid, whereby the monomer liquid reservoir is pushable into the cement powder through a further motion of the conveying plunger into the cartridge, whereby the second hollow space is progressively reduced in size in the process and whereby the monomer liquid reservoir is free or essentially free of gas and/or air inclusions provided the device is oriented appropriately. In order to push the monomer liquid contained in the second hollow space into the cement powder and in order to extrude the ready-made bone cement dough, it is sufficient to push the conveying plunger in the direction of the dispensing opening. In this context, the conducting means closes initially. Subsequently, the monomer liquid is transferred into the first hollow space with the cement powder and then the bone cement dough thus produced can be expelled from the cartridge by propelling the conveying plunger jointly with the dispensing plunger. Providing the tapering depression in the rear side of the dispensing plunger allows gases or air to collect at the feedthrough, when the device is held with the cartridge head upwards, such that the gas or air is pushable through the feedthrough into the first hollow space and, from there, rises to the dispensing opening due to the trailing monomer liquid and is pushable out through the dispensing opening. A bone cement dough that is depleted or free of bubbles can be produced by this means. Since the density of the gas is lower than that of the monomer liquid, the gas rises in the depression that tapers toward the feedthrough and, due to the orientation of the device, the tapering depression acts as a separator for the monomer liquid and an included gas. Due to the tapering shape, no gas pocket can form and no bubbles are retained. Specifically referring to a cone-shape, it is not necessary to hold the device exactly perpendicular with the cartridge head upwards as long as only the feedthrough is arranged at the highest site of the cone-shaped and/or funnel-shaped tapering depression and no other vaults are formed, in which gas bubbles could be retained.

In one embodiment, the monomer liquid can beforehand be conducted from a container, which is attached to the rear side of the conveying plunger and is connected to the fluid opening, through the conducting means into the second hollow space. In this context, the conveying plunger is pushable in the internal space of the cartridge in the direction of the dispensing opening through inserting and/or screwing the container into the cartridge. Particularly in one embodiment, a monomer liquid container is openable within the container beforehand in order to release the monomer liquid within the container. The essential advantages a device according to one embodiment are that the two starting components of the bone cement dough are stored in the closed cementing system and that the mixing of the starting components takes place in the closed device. This means that the user does not need to fill the device. This then constitutes a full-prepacked mixing system. The medical user is not at all exposed to the individual starting components of the bone cement dough. As a result, the unpleasant odour is minimised.

It is a particular advantage of the device that the monomer liquid is pressed into the cement powder by simply moving the conveying plunger forward while the conducting means stays closed. In the process, the air present between the cement powder particles is displaced by the monomer liquid. A homogeneous bone cement dough is produced without any need for any manual mixing with mixing rods with mixing vanes. This means that the error-prone manual mixing is no longer required. This requires the use of a cement powder that is adjusted appropriately such that it is wetted very well by the monomer liquid and can aspirate the monomer liquid through capillary action. The operation of the device is maximally simplified.

The advantages of devices and methods according to one embodiment are basically based on generally known linear motions being utilised to perform the monomer transfer and to close the second hollow space towards the outside.

The device can be used as a hygienic disposable product since it can be manufactured largely from plastics and since all parts including the internal spaces and the cement powder can be sterilised with ethylene oxide.

An exemplary and preferred device according to one embodiment for the storing, mixing, and dispensing of polymethylmethacrylate bone cement can include:

a) a hollow cylinder-shaped cartridge;

b) a cartridge head that closes the cartridge, whereby the cartridge head comprises an outlet opening that connects the internal space of the cartridge to the surroundings;

c) a gas-permeable and powder particle-impermeable stopper as cartridge closure that is detachably arranged in the outlet opening of the cartridge head;

d) a dispensing plunger that is arranged in the internal space of the cartridge such as to be axially mobile, whereby at least a part of the rear side of the dispensing plunger is provided in the form of a hollow cone that merges into an opening that is impermeable to powder particles and permeable to gases and liquids, and connects the front side and the rear side of the dispensing plunger in gas- and liquid-permeable manner;

e) cement powder that is arranged in a first hollow space of the cartridge that is bordered by the cartridge head with the cartridge closure, the internal wall of the cartridge, and the dispensing plunger;

f) a liquid- and gas-impermeable conveying plunger that is arranged behind the dispensing plunger in the internal space of the cartridge, whereby the front side of the conveying plunger that faces away from the dispensing plunger is cambered, and whereby the front side of the conveying plunger is shaped as a cone, whereby the cone has the same base diameter and the same slope as the hollow cone of the dispensing plunger;

g) a second hollow space that is bordered by the dispensing plunger, the internal wall of the cartridge, and the conveying plunger;

h) at least one groove extending axially on the internal side of the cartridge that has an axial extension that is longer than the axial extension of the conveying plunger, whereby the groove projects, at least partially, into the second hollow space;

i) a hollow cylinder-shaped ampoule holder as container that is arranged, at least partially, in the internal space of the cartridge, whereby the external side of the ampoule holder possesses no external thread in a first section that originates from a front side that faces the cartridge head, and possesses an external thread in a second section, whereby the ampoule holder in one embodiment is closed on its front side that faces the cartridge head by means of a sieve plate and a pore disk that is permeable to liquid and gases and impermeable to powder particles, and whereby the front face of the sieve plate pointing to the internal space of the ampoule holder possesses at least one puncturing mandrel;

j) an opening means on the ampoule holder that includes a cap with an internal thread, and whereby the internal thread of the opening means engages the external thread of the ampoule holder;

k) a sleeve that can be axially shifted in the ampoule holder and is arranged between a monomer liquid container in the ampoule holder or the opening means, and which can be axially shifted with the opening means against the monomer liquid container;

l) an internal thread on an end of the cartridge opposite from the cartridge head; whereby m) whereby the conveying plunger is shiftable appropriately over the at least one axial groove by moving the ampoule holder in the direction of the cartridge head, such that the second hollow space is closed in the direction of the ampoule holder in liquid-impermeable manner.

In one embodiment, the hollow cylinder-shaped ampoule holder is axially mobile in the cartridge, whereby the front side of the ampoule holder that faces the cartridge head is provided as conveying plunger in the shape of a cone.

The device according to one embodiment can be used advantageously by the user since the user only needs to screw-in the closure head of the ampoule holder and rotate the device such that the cartridge head faces upwards to obtain a ready-mixed bone cement dough after a few seconds that contains no or hardly any air inclusions. The processes of opening the monomer liquid container, monomer transfer, and mixing proceed in order and automatically simply by repeatedly rotating the closure head of the ampoule holder with the ampoule holder connected to it and through suitably orienting the device. Accordingly, the user errors during the opening of the monomer liquid container, the monomer transfer, and the mixing of the monomer liquid with the cement powder known from prior cementing technology are excluded by the design features. This increases the user safety significantly. The device can easily be used by untrained personnel in this context.

A method according to one embodiment can be implemented, for example, with the exemplary device for mixing of the cement powder and the monomer liquid while producing bone cement dough. An exemplary method that is preferred according to one embodiment can be implemented with the following steps proceeding in the order given:

positioning or holding the cartridge with the cartridge head downward;

rotating the closure head onto the external thread of the ampoule holder;

shifting the sleeve against the monomer liquid container;

moving the monomer liquid container against the puncturing mandrel;

opening the monomer liquid container;

monomer liquid flowing from the monomer liquid container through the at least one groove into the second hollow space and in one embodiment, if applicable, earlier also through the sieve plate and the pore disk along the camber of the conveying plunger;

shifting of the ampoule holder in the direction of the cartridge head until the external thread of the ampoule holder engages the internal thread of the cartridge, whereby the conveying plunger is simultaneously being pushed appropriately in the direction of the cartridge head such that the conveying plunger is pushed over the at least one groove and the second hollow space is closed in the direction of the ampoule holder in liquid-impermeable manner.

inverting the device such that the cartridge head points upwards;

screwing the ampoule holder into the cartridge, whereby the external thread of the ampoule holder rotates into the internal thread of the cartridge and the ampoule holder is being moved in the direction of the cartridge head;

moving the conveying plunger in the direction of the cartridge head;

extruding the monomer liquid from the second hollow space through the hollow cone in the dispensing plunger into the compacted cement powder;

wetting of the cement powder by the monomer liquid;

production of the bone cement dough by swelling of the monomer liquid-wetted cement powder;

extruding all of the monomer liquid from the second hollow space by inserting the cone of the conveying plunger into the hollow cone of the dispensing plunger;

monomer liquid displacing the air between the cement powder particles;

air escaping through the cartridge closure into the surroundings;

removing the cartridge closure after production of the cement dough;

rotating the ampoule holder in the direction of the cartridge head; and in one embodiment extruding the bone cement dough by moving the ampoule holder in the direction of the cartridge head.

Moreover, a second method is preferred according to one embodiment. The method for the mixing and dispensing of polymethylmethacrylate bone cement using the exemplary device according to one embodiment is characterized by the following steps proceeding in the order given:

positioning or holding the cartridge with the cartridge head downward;

rotating the closure head onto the external thread of the ampoule holder;

shifting the sleeve against the monomer liquid container;

moving the monomer liquid container against the puncturing mandrel;

opening the monomer liquid container;

monomer liquid flowing from the monomer liquid container through the at least one groove into the second hollow space and in one embodiment, if applicable, earlier also through the sieve plate and the pore disk along the camber of the conveying plunger;

shifting of the ampoule holder in the direction of the cartridge head until the external thread of the ampoule holder engages the internal thread of the cartridge, whereby the conveying plunger is simultaneously being pushed appropriately in the direction of the cartridge head such that the conveying plunger is pushed over the at least one groove and the second hollow space is closed in the direction of the ampoule holder in liquid-impermeable manner.

inverting the device such that the cartridge head points upwards;

moving the conveying plunger in the direction of the cartridge head;

compressing the air above the monomer liquid;

the compressed air and the compressed monomer liquid or an ejector on the conveying plunger pushing the closure out of an opening in the dispensing plunger;

the air escaping through the hollow cone into the opening of the dispensing plunger and subsequently extruding the monomer liquid through the opening of the dispensing plunger;

extruding the monomer liquid from the second hollow space through the hollow cone in the dispensing plunger into the compacted cement powder;

wetting of the cement powder by the monomer liquid;

production of the bone cement dough by swelling of the monomer liquid-wetted cement powder;

extruding all of the monomer liquid from the second hollow space by inserting the cone of the conveying plunger into the hollow cone of the dispensing plunger;

monomer liquid displacing the air between the cement powder particles;

air escaping through the cartridge closure into the surroundings;

removing the cartridge closure after production of the cement dough;

rotating the ampoule holder in the direction of the cartridge head; and in one embodiment extruding the bone cement dough by moving the ampoule holder in the direction of the cartridge head.

A variant of both exemplary methods is characterized by the following steps proceeding in the order given such that, when the mobile stopper is shifted, a coloured pin connected to the mobile stopper as marker means comes to the fore and thus indicates to the medical user that the mixing of the cement powder with the monomer liquid has taken place.

It is to be understood that the features of the various exemplary embodiments described herein may be combined with each other, unless specifically noted otherwise. FIGS. 1 to 9 illustrate depictions of a device according to one embodiment. FIGS. 1 to 4 and 7 to 9 illustrate various schematic total views of the exemplary device according to one embodiment. FIGS. 5 and 6 illustrates schematic cross-sectional views as detail views in the form of detail magnifications through a region of the device according to one embodiment. In this context, FIGS. 1 to 3 illustrate the first device according to one embodiment in a starting state or storage state, whereas FIGS. 4 to 9 illustrate cross-sectional views of the first device according to one embodiment during the use of the device in order to illustrate an exemplary method according to one embodiment.

According to an exemplary embodiment, the device has a tube-shaped cartridge 1 made of a plastic material with a cylindrical internal space. The cartridge 1 can be closed on its front side by a funnel-shaped cartridge head 2 made of plastics. The front side of the cartridge 1 is illustrated on the bottom in FIGS. 1 to 5 and 8 and 9 and on the top in FIGS. 6 and 7 allowing air or gas to escape from the device in upward direction. The tip of the funnel-shaped cartridge head 2 can have a central dispensing opening arranged on it, which can initially be closed in the starting state. According to an alternative embodiment, the cartridge head 2 can just as well be a flat cap or have a different shape. However, in order to prevent air or gas inclusions in the area of the cartridge head, a funnel-shaped cartridge head 2 is preferred according to one embodiment. It is basically feasible just as well to provide the cartridge head 2 and the cartridge 1 as a single part. However, in order to simplify the assembly of the device, it is preferred that the cartridge head 2 is connected to the cartridge 1 in the form of a separate part, for example is screwed or plugged onto it.

According to another embodiment, a rear side of the cartridge 1 opposite from the front side of the cartridge 1 can have a conveying plunger 3 arranged in the internal space of the cartridge 1 that is supported in the internal space of the cartridge 1 such as to be axially mobile in the direction of the front side of the cartridge 1. A dispensing plunger 4 can be arranged between the conveying plunger 3 and the front side of the cartridge 1. The conveying plunger 3 and the dispensing plunger 4 can be manufactured from plastics, at least in part. A first hollow space 60 is formed on the inside of the device (see FIG. 2) between the dispensing plunger 4 and the front side of the cartridge 1 and/or the cartridge head 2. The first hollow space 60 can contain a cement powder 5 as one of the starting components of the bone cement dough 62 to be produced (see FIGS. 7 to 9). In one embodiment, the cement powder 5 is pressed in or at least stored in compact form in the cartridge head 2 between the dispensing plunger 4 and the cartridge head 2 and in the internal space of the cartridge 1 in the first hollow space 60 in order to simplify the introduction and distribution of a monomer liquid 6 in the cement powder 5 through the use of capillary forces between the cement powder particles.

The dispensing plunger 4 and the conveying plunger 3 and the internal walls of the cartridge 1 can border a second hollow space 7 in the internal space of the cartridge 1. The internal wall of the cartridge 1 can have multiple grooves arranged on it as conducting means 8 that is permeable to the monomer liquid 6 and through which the monomer liquid 6 can be conducted into the second hollow space 7. The grooves and/or the conducting means 8 can extend in axial direction of the internal space of the cartridge 1. The grooves are preferred not to extend into the first hollow space 60. The grooves can be situated at a distance from each other in radial direction at various angles. The dispensing plunger 4 can have a feedthrough 9 provided in it that commences on the tip of a funnel-shaped depression and through which the monomer liquid 6 can flow or be conducted from the second hollow space 7 to the cement powder 5 in the first hollow space 60 (see FIG. 6).

The dispensing plunger 4 can include, on its rear side, a funnel-shaped surface 44 that corresponds to a negative form with respect to a cone-shaped surface 46 on the front side of the conveying plunger 3. In this context, one embodiment can provide the dispensing plunger 4 to be able to touch by its funnel-shaped surface 44 against the cone-shaped surface 46 of the conveying plunger 3 by matching surfaces, when the conveying plunger 3 is pushed against the dispensing plunger 4 (see FIGS. 7 to 9). In this context, the volume of the second hollow space 7 can be reduced to zero such that the second hollow space 7 is disappeared in this state.

One embodiment can provide a pin 10 in the form of a cylindrical pin to be arranged on the tip of the cone-shaped surface 46 on the rear side of the dispensing plunger 3. In this context, the external circumference of the pin 10 can be somewhat smaller than the feedthrough 9 such that the feedthrough 9 is not closed in liquid-tight manner by the pin 10. For this purpose, the external circumference of the pin 10 can be somewhat smaller than the internal circumference of the feedthrough 9.

According to a development of the present exemplary embodiment, a stopper (not illustrated) that initially closes the feedthrough 9 in gas-tight and liquid-tight manner in the storage state and/or starting state can be arranged in the feedthrough 9. The stopper in the feedthrough 9 is pushable out of the feedthrough 9 by the pin 10 in order to open the feedthrough 9 towards the first hollow space 60. In this context, the pin 10 can have an appropriate longitudinal extension such that it encounters the stopper in the feedthrough 9 once the distance between the dispensing plunger 4 and the conveying plunger 3 is less than a minimum distance, whereby the conducting means 8 is already closed with respect to the second hollow space 7 by the conveying plunger 3 in the position of the conveying plunger 3. By this means, the second hollow space 7 is closed outwards with respect to a rear-side part 11 of the internal space of the cartridge 1, before the feedthrough 9 of the second hollow space 7 is being opened with respect to the first hollow space 60. The pin 10 can in one embodiment be pushed through the feedthrough 9 when the conveying plunger 3 is pushed in the direction of the dispensing plunger 4.

According to another embodiment, the feedthrough 9 and the pin 10 can be arranged along or parallel to the cylinder axis of the cylindrical internal space of the cartridge 1 or be aligned with each other.

To an informed expert it is clear in this context that this embodiment with a central feedthrough in the dispensing plunger 4 can easily be applied to a non-central fluid opening as well. Likewise, a pin that is not arranged on the cylinder axis of the internal space of the cartridge 1 can be implemented. Likewise, multiple pins can easily be arranged on the front side of the conveying plunger 4.

Moreover, rather than many grooves, just a single groove can be provided as conducting means 8 for conducting the monomer liquid 6 from the rear-side part 11 of the internal space of the cartridge 1 into the second hollow space 7. Likewise, the conducting means 8 can just as well be realized by at least one liquid-permeable line that originates in the area of the rear-side part 11 of the internal space of the cartridge 1 and merges into the second hollow space 7 upstream of the conveying plunger 3 in the starting state (FIG. 1), whereby the merging site into the second hollow space 7 can have the conveying plunger 3 travel over it and thus close it with respect to the second hollow space 7 in liquid-tight manner. The conducting means 8 can then be realized by hoses or bore holes in the wall of the cartridge 1. It is an important and central aspect for the implementation of the present embodiment that all connections of the conducting means 8 to the second hollow space 7 are closed by the conveying plunger 3 by propelling the conveying plunger 3 in the direction of the cartridge head 2, and subsequently the conveying plunger 3 and the dispensing plunger 4 are driven towards each other, then in one embodiment touch against each other, and the volume of the second hollow space 7 is reduced to zero, when the conveying plunger 3 is driven further in the direction of the dispensing plunger 4. Based on this aspect, a person skilled in the art can easily find conducting means 8 that are similar or equal in effect and shall be considered to be included in the scope of the present embodiment.

The dispensing opening in the cartridge head 2 can initially be closed by a stopper 12 (see FIGS. 1 to 4 and 7). The stopper 12 can have a passage arranged in it through which gases can be evacuated from and conducted into the first hollow space 60. In order to prevent cement powder 5 from leaking, one embodiment can provide a pore filter 14 that is impermeable to the cement powder 5, but is permeable to gases, to be arranged in the passage. A coloured marker means 16 can be provided on the stopper 12 in the form of a coloured tube that allows a motion of the stopper 12 against the dispensing opening to be recognized visually. For this purpose, the coloured marker means 16 can for example be red or of any other signal colour. However, other (including non-visual) methods are conceivable that indicate a motion of the stopper 12 against the dispensing opening to the user.

The cartridge head 2 can have a wing screw 20 arranged on it by means of which the stopper 12 is attached in detachable manner in the dispensing opening. The wing screw 20 can have a bore hole provided in it, in which the stopper 12 can be mobile with respect to the wing screw 20. As soon as the marker means 16 (i.e. the tube) is pushed forward out of the wing screw 20, the user of the device can recognise that the bone cement dough 62 is ready for use, since the cement powder 5 cannot transfer a pressure transferred from the dispensing plunger 4 to the pore filter 14 and the stopper 12 as long as it is not wetted by the monomer liquid and behaves like a fluid.

In order to prevent leakage of monomer liquid 6 and bone cement dough 62 and/or to seal the first hollow space 20 from the second hollow space 7 or other areas from each other, seals can be provided. Accordingly, two sealing rings 22 can be arranged in two circumferential grooves on an external circumference of the stopper 12 for sealing with respect to the wing screw 20. A sealing ring 24 can be provided to be arranged in a circumferential groove on the external side of the cartridge 1 and to seal the cartridge head 2 with respect to the cartridge 1. Two sealing rings 26 can be arranged in two circumferential grooves on the external circumference of the dispensing plunger 4 to seal the dispensing plunger 4 with respect to the internal wall of the cartridge 1. Two sealing rings 28 can be arranged in two circumferential grooves on the external circumference of the conveying plunger 3 to seal the conveying plunger 3 and the container 34 with respect to the internal wall of the cartridge 1. Two sealing rings 29 can be arranged in two circumferential grooves on the external circumference of the container 34 that can be arranged on the rear side of the conveying plunger 3, whereby the sealing rings 29 seal the container 34 with respect to the internal wall of the cartridge 1.

A socket 30 that surrounds the dispensing opening can be provided on the tip of the cartridge head 2. The socket 30 can have an internal thread provided in it, into which a dispensing tube 64 (see FIGS. 8 and 9) with a matching external thread can be screwed. The wing screw 20 can be detachably attached to the socket 30 in the same internal thread or on a different attachment means of the socket 30 by means of a matching external thread or a different matching counter attachment means.

In order to obtain a complete full-prepacked mixing system, a monomer liquid container 32, for example in the form of an ampoule made of glass or plastics that can be fractured, can be arranged in the container 34, which can be arranged on or attached to the rear side of the conveying plunger 3 for this purpose. For example, the container 34 can be attached to the conveying plunger 3 with a screw, a rivet or a bolt, as is illustrated in FIGS. 1, 2, and 4 to 9. The monomer liquid container 32 can contain the monomer liquid 6. The internal space of the container 34 can be connected to the rear-side part 11 of the internal space of the cartridge 1 in liquid-permeable manner by means of at least one monomer line 35. A sieve and/or a pore filter can be arranged at the merging sites of the internal space of the container 34 to the at least one monomer line 35, by means of which fragments of the monomer liquid container 32 can be retained. In turn, the rear-site part 11 of the internal space of the cartridge 1 can be connected to the second hollow space 7 in liquid-permeable manner by means of the conducting means 8 (the grooves in the internal wall of the cartridge). A monomer liquid 6 released in the container 34 can flow from the container 34 into the second hollow space 7, when the device is held or set up with the cartridge head 2 downwards.

A ring sleeve 36 with an internal thread can be attached to a rear-side end of the cartridge 1 that is opposite from the cartridge head 2. This simplifies the assembly of the device provided it is present as a part that is separate from cartridge 1. For this purpose, the ring sleeve 36 can be screwed into an internal thread on the rear-side end of the cartridge 1 by means of a matching external thread.

According to a preferred development, one embodiment can provide the container 34 to include an external thread on its external circumference. Particularly in one embodiment, the external thread matches the internal thread of the ring sleeve 36 or an internal thread on the rear-side end of the cartridge 1. By this means, the container 34 can be screwed into the cartridge 1. This can enable a propulsion of the conveying plunger 3 in the internal space of the cartridge 1. Theoretically, as an alternative to the container 34, a cylinder (not illustrated) with a matching external thread can be attached to or loosely arranged on the rear side of the conveying plunger 3 such that the conveying plunger 3 and, by means of the conveying plunger 3, the dispensing plunger 4 as well is pushable inside the internal space of the cartridge 1 in the direction of the cartridge head 2 by the cylinder being screwed in. A front part of the container 34 that faces the cartridge head 2 is preferred to have no external thread and can thus be inserted into the ring sleeve 36 and thus into the internal space of the cartridge 1 until the external thread of the container 34 encounters the internal thread on the ring sleeve 36. The length of the section of the container 34 with no external thread and the length of the conducting means 8 can in one embodiment be matched appropriately such that the conveying plunger 3 seals the at least one conducting means 8 with respect to the second hollow space 7, before the external thread of the container 34 engages the internal thread of the ring sleeve 36 and/or of the cartridge 1.

In order to prevent the container 34 and/or the ring sleeve 36 from moving prematurely or inadvertently against the cartridge 1, a detachable locking means (not illustrated) can be provided. An opening means 50 for opening the monomer liquid container 32 can be arranged on a rear side of the container 34 that faces away from the cartridge head 2. In order to prevent the monomer liquid container 32 from being opened inadvertently, a locking means 38 that can be pulled off can be provided. For this purpose, the locking means 38 can be shaped like a brace that engages on the external circumference of the container 34 or a different rear-side extension of the conveying plunger 3 and rests on a front side end of the opening means 50.

One embodiment can provide a pore filter 40 to be arranged in or on the dispensing plunger 4. The feedthrough 9 can be covered by the pore filter 40. This prevents cement powder 5 from the first hollow space 60 from penetrating into the feedthrough 9 or into the second hollow space 7, where it would form a gel-like barrier upon reaction with the monomer liquid 6 and thus counteract a distribution of the monomer liquid 6 in the cement powder 5.

The pore filter 40 can in one embodiment be a circular disk. The pore filter 40 can be covered by a disk 42 and can be attached in the dispensing plunger 4. To enable and/or facilitate the monomer liquid 6 being conducted through and distributed in the first hollow space 60 and in the cement powder 5, a multitude of boreholes or holes can be provided in the disk 42 (see FIG. 2).

A pin 48 or a puncturing mandrel or a sheath can be arranged in the internal space of the container 34. The pin 48, the puncturing mandrel or the sheath can touch against a cartridge base 58 of the monomer liquid container 32 and can be used to fracture the monomer liquid container 32 at the cartridge base 58 or to puncture or cut open a monomer liquid container 32. In one embodiment, the pin 48 can be arranged in the area of the merging site into the monomer line 35.

The opening means 50 for opening the monomer liquid container 32 can be arranged on the rear side of the container 34 that faces away from the conveying plunger 3. The opening means 50 can include a manually operated handle 52 and a cap 54 for this purpose. One embodiment can provide the cap 54 to be supported against the container 34 such as to be mobile, whereby the cap 54 can in one embodiment be screwed onto the external thread of the container 34. The container 34 can be open on its rear side. On the inside of the container 34, a sleeve 56 in the form of a piece of tube can be supported against the container 34 such as to be mobile as part of the opening means 50. The monomer liquid container 32 is openable inside the container 34 through a motion of the sleeve 56 into the container 34. In one embodiment, an ampoule as monomer liquid container 32 is pushed appropriately onto the pin 48 by the cartridge base 58 such that the cartridge base 58 fractures or breaks off and the ampoule is thus opened (see FIG. 4). By this means, the monomer liquid 6 can be released from the monomer liquid container 32 on the inside of the container 34.

The work-flow of a method according to one embodiment is illustrated in the following based on FIGS. 1 to 9 using the device according to one embodiment for an example.

The device is initially in the original state or storage state illustrated in FIGS. 1 to 3. In this state, the device can be evacuated through suitable openings and can be sterilised with ethylene oxide.

Next, the device can be held with the cartridge lid 2 downwards. Then, the locking means 38 can be pulled off. Then the opening means 50 can be screwed onto the container 34, until the cartridge base 58 of the monomer liquid container 32 fractures. Due to the monomer liquid container 32 fracturing, the monomer liquid 6 contained therein is released and can flow from the container 34 through the at least one monomer line 35, through the rear-site part 11 of the internal space of the cartridge 1, and through the conducting means 8 into the second hollow space 7. This situation is illustrated in FIG. 4.

Subsequently, the locking element, if present, can be pulled off. The container 34 can now the inserted more deeply into the cartridge 1, until the external thread on the container 34 encounters the internal thread on the ring sleeve 36 and blocks the container 34 from moving further into the cartridge 1. This situation is illustrated in FIG. 5. All or most of the monomer liquid 6 has already flown into the second hollow space 7 by then. The conveying plunger 3 is already pushed so far over the conducting means 8 in this situation that the conveying plunger 3 seals the connection of the conducting means 8 into the second hollow space 7.

In this situation, the device can be inverted such that the cartridge head 12 points upwards or approximately upwards (for example points upwards with an angle of less than 50° to the perpendicular). The device can then be held with the cartridge head 2 upwards to allow gas inclusions and/or air inclusions to escape and be extruded from the second hollow space 7 through the feedthrough 9 and through the cement powder 5 in the first hollow space 60 upwards through the stopper 12 of the device. Due to the funnel-shaped surface 44 on the rear-side of the dispensing plunger 4, gas and/or air inclusions collect in the tip thereof and can thus be easily and readily pressed through the feedthrough 9 in the dispensing plunger 4 into the first hollow space 60 by pushing the conveying plunger 3 in the direction of the dispensing plunger 4. Along with the container 34, the conveying plunger 3 can also be pushed in the direction of the dispensing plunger 4 in the internal space of the cartridge 1. The volume of the second hollow space 7 is reducible through the motion of the conveying plunger 3 in the direction of the dispensing plunger 4.

The ring sleeve 36 can now be screwed upwards, away from the cartridge head 10 of the cartridge 1, until the internal thread of the ring sleeve 36 engages the external thread of the container 34. Meanwhile, the monomer liquid 6 can already begin to flow through the feedthrough 9 in the dispensing plunger 4 and, if applicable, through the pore disk 40 and the disk 42 into the second hollow space 60. This situation is depicted in FIG. 6, in which the device is rotated by 180° compared to FIG. 5, such that the cartridge head 2 (not illustrated in FIGS. 5 and 6) is aligned upwards in order to enable and/or facilitate the escape of gas or air from the first hollow space 60 and the second hollow space 7. In order not to have to hold the device exactly perpendicular with the cartridge head 2 upwards, the funnel-shaped surface 44 has a sufficiently steep slope (more than 45°) such that an upward slope to the feedthrough 9 still exists if the position of the cartridge 1 is inclined by 45° such that gas inclusions and/or air bubbles in the funnel-shaped surface 44 rise upwards to the feedthrough 9 and escape there from the second hollow space 7 through the feedthrough 9 into the first hollow space 60. The trailing monomer liquid 6 drives the gas and/or the air from there through the powder particles of the cement powder 5 and through the pore filter 14 out of the device.

Once the monomer liquid 6 flows into the first hollow space 60, it becomes distributed between the powder particles of the cement powder 5 and thus in the cement powder 5 due to capillary forces. In this context, gas and/or air in the intervening spaces between the polymer particles of the cement powder 5 can be displaced from the cement powder 5 in upward direction and can escape through the dispensing opening through the gas-permeable pore filter 14. Then, the container 34 can be screwed more deeply into the cartridge 1 by rotating the container 34 against the ring sleeve 36 and/or against the cartridge 1.

The container 34 can now be screwed even more deeply into the cartridge 1. The monomer liquid 6 is pressed from the second hollow space 7 into the cement powder 5 in the first hollow space 60 and becomes distributed therein in this context. Lastly, the conveying plunger 3 can encounter the dispensing plunger 4 such that the cone-shaped surface 46 of the conveying plunger 3 touches against the matching final-shaped surface 44 on the rear side of the dispensing plunger 4, in one embodiment touching against it with matching surfaces. In the meantime, the cement powder 5 exposed to the monomer liquid 6 swells and produces the bubble-free or bubble-depleted bone cement dough 62.

The container 32 can be screwed even more deeply into the cartridge 1, when the bone cement 62 is produced up to the dispensing opening and/or when the cement powder 5 is wetted by the monomer liquid 6 all the way up to the dispensing opening, since only then a flowable material is obtained in the first hollow space 60 that can be pushed into the dispensing opening. The stopper 12 can be moved in the dispensing opening through the motion of the bone cement dough 62. This can be recognized visually through a shift of the marker means 16 out of the stopper 12 such that the user is aware that the bone cement dough 62 is now ready for use. This situation is illustrated in FIG. 7.

Next, the wing screw 20 with the stopper 12 can be unscrewed from the dispensing opening. Then, the dispensing tube 64 can be screwed into the socket 30. As soon as the protruding stopper 12 indicates that the bone cement dough 62 is ready for use, the device can be turned around again and/or can be held in any position, since the air and/or gas inclusions have now escaped from the first hollow space 60 and a bubble-free bone cement dough 62 can thus be produced. Subsequently, the bone cement dough 62 can be dispensed from the dispensing opening by screwing the container 34 further in and thus by further propelling the conveying plunger 3 and the dispensing plunger 4 in the direction of the dispensing opening. This situation is illustrated in FIG. 8, in which the device is illustrated to be held with the cartridge head 2 downwards again. The bone cement dough 62 can be expelled by screwing the container 34 further into the cartridge 1, in that the conveying plunger 3 and the dispensing plunger 4 are driven by the motion of the container until the dispensing plunger 4 encounters the cartridge head 2. This situation is illustrated in FIG. 9. Due to the cone-shaped depression in the cartridge head 2, a dead volume can arise in the cartridge head 2, in which a part of the bone cement dough 62 is retained. Due to elastic properties of the device, minor amounts of the monomer liquid 6 may be pressed into this section at the end of the extrusion process. Having the dead volume can prevent this part of the bone cement dough 62, which has a somewhat different consistency from the rest of the bone cement dough 62, from being retained in the device.

The features of the embodiments disclosed in the preceding description and in the claims, figures, and exemplary embodiments, can be essential for the implementation of the various embodiments both alone and in any combination.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:
1. A device for the production of a bone cement dough from a monomer liquid and a cement powder as starting components of the bone cement dough, and for dispensing of the bone cement dough, the device comprising
 a cartridge with a cylindrical internal space;
 a cartridge head with a dispensing opening for dispensing the bone cement dough, whereby the cartridge head closes the cartridge on a front side of the cartridge except for the dispensing opening;
 a conveying plunger that is arranged in the internal space of the cartridge and is supported in the internal space of the cartridge such that it is pushable in the direction of the dispensing opening;
 a dispensing plunger that is arranged in the internal space of the cartridge between the dispensing opening and the conveying plunger and that is supported in the internal space of the cartridge such that it is pushable in the direction of the dispensing opening, whereby a rear side of the dispensing plunger facing the conveying plunger comprises a tapering depression that tapers in the direction of the cartridge head;
 a first hollow space that is bordered by the cartridge head, by internal walls of the cartridge, and by the dispensing plunger, whereby a cement powder is arranged in the first hollow space;
 a second hollow space that is part of the cylindrical internal space of the cartridge, whereby the second hollow space is bordered by the dispensing plunger and the conveying plunger;

a rear-side part of the internal space of the cartridge, whose front side is bordered by a rear side of the conveying plunger that faces away from the dispensing plunger;

a conducting means, which connects the second hollow space to the rear-side part of the internal space of the cartridge, by-passing the conveying plunger, such as to be permeable to the monomer liquid, whereby the conducting means is closable by the conveying plunger with respect to the second hollow space through a shift of the conveying plunger in the direction of the dispensing plunger; and a feedthrough, whereby the feedthrough commences at a tip of the tapering depression, extends through the dispensing plunger and connects the first hollow space and the second hollow space such as to be permeable to the monomer liquid, but impermeable to the cement powder.

2. The device according to claim 1, wherein a front side of the conveying plunger that faces the dispensing plunger comprises a surface that projects in the direction of the dispensing plunger.

3. The device according to claim 1, wherein the tapering depression that tapers in the direction of the cartridge head is a depression in the form of a funnel-shaped surface that tapers steadily originating from the internal wall of the cartridge, whereby a projecting surface on the front side of the conveying plunger can be inserted into the funnel-shaped surface on the rear side of the dispensing plunger, whereby the feedthrough in the dispensing plunger merges into the dispensing plunger at the lowest site of the funnel-shaped surface.

4. The device according to claim 1, wherein a front side of the conveying plunger that faces the dispensing plunger and the rear side of the dispensing plunger that faces the conveying plunger are shaped with matching surfaces with respect to each other such that the front side of the conveying plunger touches against the rear side of the dispensing plunger with matching surfaces, when the conveying plunger is pushed against the dispensing plunger, whereby the volume of the second hollow space thereby is reducible to a maximum of 1% of the volume of the second hollow space in a starting state.

5. The device according to claim 1, wherein the rear side of the dispensing plunger that faces the conveying plunger comprises a funnel-shaped surface as the tapering depression that has the feedthrough arranged in its lowest site, and a front side of the conveying plunger that faces the dispensing plunger comprises a projecting cone-shaped surface with the same slope as the funnel-shaped surface on the rear side of the dispensing plunger, whereby a cylindrical pin that is insertable into a cylindrical depression as part of the feedthrough in the dispensing plunger is arranged on the tip of the projecting cone-shaped surface on the front side of the conveying plunger.

6. The device according to claim 5, wherein the funnel-shaped surface on the rear side of the dispensing plunger comprises an angle of slope of at least 60°, and the cone-shaped surface on the front side of the conveying plunger comprises a matching angle of slope of at least 60°.

7. The device according to claim 1, wherein a container is arranged on the rear side of the conveying plunger, with a monomer liquid container containing the monomer liquid being arranged in the container, which is an ampoule made of glass or plastics, whereby the monomer liquid container is openable inside the container and whereby the container is connected to the rear-side part of the internal space of the cartridge in liquid-permeable manner by means of at least one monomer line, whereby an opening means is arranged on a side of the container opposite from the conveying plunger, by means of which the monomer liquid container is openable inside the container, whereby the opening means is a sleeve attached to a cap, whereby the cap is screwable onto a thread of the container and the cap comprises a counter-thread for this purpose such that, when the cap is being screwed on, the ampoule is pushed, by the sleeve, onto at least one projecting pin on the inside of the container and thus the monomer liquid container is breakable open.

8. The device according to claim 7, wherein the container comprises an external thread that is screwable into an internal thread on an end of the cartridge opposite from the cartridge head, whereby the conveying plunger is pushable in the direction of the dispensing opening by screwing the container into the cartridge, and the dispensing plunger is pushable by the conveying plunger in the direction of the dispensing opening, whereby the internal thread is part of a ring sleeve that is connected to the cartridge on the end of the cartridge opposite from the cartridge head.

9. The device according to claim 7, wherein the external side of the container possesses no external thread in a first section that originates from a front side that faces the cartridge head, and possesses an external thread in a second section.

10. The device according to claim 1, wherein the conducting means terminates or merges at a site on the internal wall of the cartridge that is situated at an appropriate axial distance from the dispensing plunger relative to the axis of the cylindrical internal space, such that the volume of the second hollow space is at least equal to the volume of the monomer liquid conducted into it through the conducting means, when the conveying plunger is pushed just far enough in the direction of the dispensing plunger such that the conveying plunger closes the conducting means with respect to the second hollow space.

11. The device according to claim 1, wherein the dispensing opening has a stopper arranged in it that closes the dispensing opening impermeable to the cement powder, wherein it closes the dispensing opening permeable to gases, whereby the stopper is arranged in the dispensing opening such as to be mobile such that the stopper is pushable out of the dispensing opening by pressing on the ready-mixed bone cement dough, whereby it has a marker means that is visible from outside attached to the stopper.

12. The device according to claim 1, wherein the feedthrough is closed by a stopper that is impermeable to gases and liquids, whereby the stopper is shiftable in the feedthrough in the direction of the cartridge head, whereby the front side of the conveying plunger has a pin arranged on it by means of which the stopper in the feedthrough is pushable out of the feedthrough and thus the feedthrough is openable, whereby the pin has an appropriate axial extension with respect to the cylindrical internal space of the cartridge such that, upon the pin and the stopper touching, the volume between the rear side of the dispensing plunger and the front side of the conveying plunger in the internal space of the cartridge is at least equal to the volume of the monomer liquid in a monomer liquid container that is arranged or is to be arranged in the device.

13. A method for the production of a bone cement dough, whereby the bone cement dough is produced from a cement powder and a monomer liquid with a device according to claim 1, comprising the following steps proceeding in the order given:

A) conducting the monomer liquid through the conducting means into the second hollow space;
B) pushing the conveying plunger in the direction of the dispensing plunger until the dispensing plunger closes all connections of the conducting means to the second hollow space;
C) holding the device with the cartridge head upwards and pushing the conveying plunger further in the direction of the dispensing plunger, whereby air or gas is removed from the first hollow space and from the second hollow space through the cartridge head, and whereby the monomer liquid is pushed from the second hollow space into the cement powder in the first hollow space; and
D) the conveying plunger pushing the dispensing plunger in the direction of the dispensing opening, whereby the bone cement dough produced in the first hollow space flows out through the dispensing opening.

14. The method according to claim 13, wherein the device is set up or held with the cartridge head downwards in step A), and in step B) as well, and, in step C), gas inclusions escape from the second hollow space through the feedthrough, the first hollow space, and the dispensing opening in the cartridge head, escape through a filter in the dispensing opening that is permeable to gases, but impermeable to the cement powder, whereby the filter closes the dispensing opening permeable for gases and impermeable for the cement powder.

15. The method according to claim 13, wherein the conveying plunger touches against the dispensing plunger in step D) with matching surfaces.

16. The method according to claim 13, wherein the pressure acting on the bone cement dough in step D) moves or pushes forward a stopper in the dispensing opening.

17. The method according to claim 13, wherein a monomer liquid container containing the monomer liquid is opened in a container before step A) and the monomer liquid is released in the container, whereby the container is arranged on a rear side of the conveying plunger that faces away from the dispensing plunger, and the monomer liquid flows from the container through the conducting means into the second hollow space in step A), whereby the conveying plunger in steps B) and C) and the conveying plunger and the dispensing plunger in step D) are driven by the container being pushed or screwed into the cartridge (1).

18. The device according to claim 2, wherein the front side of the conveying plunger that faces the dispensing plunger tapers steadily in the direction of the dispensing plunger.

19. The method according to claim 13, wherein the bone cement dough is a pasty polymethylmethacrylate bone cement dough.

20. The method according to claim 15, wherein in step C), the volume of the second hollow space is reduced completely to zero or down to a maximum of 1% of the volume of the second hollow space in a starting state.

21. The method according to claim 16, wherein the stopper is removed from the dispensing opening subsequently and then an application tube is attached to the cartridge head of the cartridge.

* * * * *